United States Patent
Kheradvar et al.

(10) Patent No.: US 9,668,859 B2
(45) Date of Patent: Jun. 6, 2017

(54) PERCUTANEOUS HEART VALVE DELIVERY SYSTEMS

(71) Applicants: CALIFORNIA INSTITUTE OF TECHNOLOGY, Pasadena, CA (US); THE REGENTS OF THE UNIVERSITY OF CALIFORNIA, Oakland, CA (US)

(72) Inventors: Arash Kheradvar, Irvine, CA (US); Gregory S. Kelley, Santee, CA (US); Morteza Gharib, Altadena, CA (US)

(73) Assignees: CALIFORNIA INSTITUTE OF TECHNOLOGY, Pasadena, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 888 days.

(21) Appl. No.: 13/862,302

(22) Filed: Apr. 12, 2013

(65) Prior Publication Data

US 2013/0310923 A1    Nov. 21, 2013

Related U.S. Application Data

(63) Continuation-in-part of application No. PCT/US2012/049645, filed on Aug. 3, 2012.
(Continued)

(51) Int. Cl.
*A61F 2/24*    (2006.01)
*A61B 8/12*    (2006.01)
(Continued)

(52) U.S. Cl.
CPC .......... *A61F 2/2439* (2013.01); *A61B 8/0841* (2013.01); *A61B 8/0891* (2013.01);
(Continued)

(58) Field of Classification Search
CPC ........ A61F 2/24; A61F 2/2427; A61F 2/2439; A61F 2/95; A61F 2002/9511; A61F 2002/9665

See application file for complete search history.

(56) References Cited

U.S. PATENT DOCUMENTS 3,153,975 A    10/1964 Rapata
3,671,979 A    6/1972 Moulopoulos
(Continued)

FOREIGN PATENT DOCUMENTS

CN    201380031016.2    4/2016
EP    0380686 A1    8/1990
(Continued)

OTHER PUBLICATIONS

Bagur, R., et al., "Usefulness of TEE as the Primary Imaging Technique to Guide Transcatheter Transapical Aortic Valve Implantation", JACC: Cardiovascular Imaging, 2011, vol. 4, No. 2, pp. 115-124.
(Continued)

*Primary Examiner* — Katherine Rodjom
(74) *Attorney, Agent, or Firm* — One LLP

(57) ABSTRACT

Embodiments described herein address the need for improved catheter devices for delivery, repositioning and/or percutaneous retrieval of the percutaneously implanted heart valves. One embodiment employs a plurality of spring-loaded arms releasably engaged with a stent frame for controlling expansion for valve deployment. Another embodiment employs a plurality of filaments passing through a distal end of a pusher sleeve and apertures in a self-expandable stent frame to control its state of deployment. With additional features, lateral positioning of the stent frame may also be controlled. Yet another embodiment includes plurality of outwardly biased arms held to complimentary stent frame features by overlying sheath segments. Still another embodiment integrates a visualization system in the subject delivery system. Variations on hardware and methods associated with the use of these embodiments are contemplated in addition to those shown and described.

22 Claims, 14 Drawing Sheets

Related U.S. Application Data

(60) Provisional application No. 61/666,657, filed on Jun. 29, 2012, provisional application No. 61/515,679, filed on Aug. 5, 2011, provisional application No. 61/732,117, filed on Nov. 30, 2012, provisional application No. 61/682,663, filed on Aug. 13, 2012, provisional application No. 61/623,410, filed on Apr. 12, 2012.

(51) Int. Cl.
*A61B 8/08* (2006.01)
*A61B 90/00* (2016.01)

(52) U.S. Cl.
CPC ............... *A61B 8/12* (2013.01); *A61B 90/37* (2016.02); *A61F 2/2427* (2013.01); *A61B 2090/3782* (2016.02)

(56) References Cited

U.S. PATENT DOCUMENTS

| | | |
|---|---|---|
| 4,291,420 A | 9/1981 | Reul |
| 4,451,936 A | 6/1984 | Carpentier et al. |
| 4,692,164 A | 9/1987 | Dzemeshkevich et al. |
| 4,759,758 A | 7/1988 | Gabbay |
| 4,787,901 A | 11/1988 | Baykut |
| 4,790,843 A | 12/1988 | Carpentier et al. |
| 4,851,001 A | 7/1989 | Taheri |
| 4,872,874 A | 10/1989 | Taheri |
| 4,935,030 A | 6/1990 | Alonso |
| 4,994,077 A | 2/1991 | Dobben |
| 5,002,567 A | 3/1991 | Bona et al. |
| 5,032,128 A | 7/1991 | Alonso |
| 5,037,434 A | 8/1991 | Lane |
| 5,080,668 A | 1/1992 | Bolz et al. |
| 5,141,491 A | 8/1992 | Bowald |
| 5,163,953 A | 11/1992 | Vince |
| 5,219,355 A | 6/1993 | Parodi et al. |
| 5,254,127 A | 10/1993 | Wholey et al. |
| 5,282,847 A | 2/1994 | Trescony et al. |
| 5,327,774 A | 7/1994 | Nguyen et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,552 A | 5/1995 | Andersen et al. |
| 5,445,626 A | 8/1995 | Gigante |
| 5,469,868 A | 11/1995 | Reger |
| 5,480,423 A | 1/1996 | Ravenscroft et al. |
| 5,500,014 A | 3/1996 | Quijano et al. |
| 5,545,214 A | 8/1996 | Stevens |
| 5,554,185 A | 9/1996 | Block et al. |
| 5,571,175 A | 11/1996 | Vanney et al. |
| 5,591,195 A | 1/1997 | Taheri et al. |
| 5,607,464 A | 3/1997 | Trescony et al. |
| 5,609,626 A | 3/1997 | Quijano et al. |
| 5,643,208 A | 7/1997 | Parodi |
| 5,693,087 A | 12/1997 | Parodi |
| 5,713,953 A | 2/1998 | Vallana et al. |
| 5,716,370 A | 2/1998 | Williamson, IV et al. |
| 5,735,859 A | 4/1998 | Fischell et al. |
| 5,741,326 A | 4/1998 | Solovay |
| 5,741,333 A | 4/1998 | Frid |
| 5,749,890 A | 5/1998 | Shaknovich |
| 5,800,506 A | 9/1998 | Perouse |
| 5,824,061 A | 10/1998 | Quijano et al. |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,879,320 A | 3/1999 | Cazenave |
| 5,895,419 A | 4/1999 | Tweden et al. |
| 5,910,170 A | 6/1999 | Reimink et al. |
| 5,925,063 A | 7/1999 | Khosravi |
| 5,931,855 A | 8/1999 | Buncke |
| 5,954,766 A | 9/1999 | Zadno-Azizi et al. |
| 5,957,949 A | 9/1999 | Leonhardt et al. |
| 6,010,531 A | 1/2000 | Donlon et al. |
| 6,042,607 A | 3/2000 | Williamson, IV et al. |
| 6,077,298 A | 6/2000 | Tu et al. |
| 6,106,550 A | 8/2000 | Magovern et al. |
| 6,106,551 A | 8/2000 | Crossett et al. |
| 6,132,473 A | 10/2000 | Williams et al. |
| 6,139,575 A | 10/2000 | Shu et al. |
| 6,168,614 B1 | 1/2001 | Andersen et al. |
| 6,206,911 B1 | 3/2001 | Milo |
| 6,283,127 B1 | 9/2001 | Sterman et al. |
| 6,287,334 B1 | 9/2001 | Moll et al. |
| 6,299,637 B1 | 10/2001 | Shaolian et al. |
| 6,312,447 B1 | 11/2001 | Grimes |
| 6,355,030 B1 | 3/2002 | Aldrich et al. |
| 6,364,904 B1 | 4/2002 | Smith et al. |
| 6,402,780 B2 | 6/2002 | Williamson, IV et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,451,054 B1 | 9/2002 | Stevens |
| 6,454,799 B1 | 9/2002 | Schreck |
| 6,458,153 B1 | 10/2002 | Bailey et al. |
| 6,461,366 B1 | 10/2002 | Seguin |
| 6,482,228 B1 | 11/2002 | Norred |
| 6,503,272 B2 | 1/2003 | Duerig et al. |
| 6,508,833 B2 | 1/2003 | Pavcnik et al. |
| 6,530,952 B2 | 3/2003 | Vesely |
| 6,564,805 B2 | 5/2003 | Garrison et al. |
| 6,569,196 B1 | 5/2003 | Vesely |
| 6,582,462 B1 | 6/2003 | Andersen et al. |
| 6,602,286 B1 | 8/2003 | Strecker |
| 6,629,534 B1 | 10/2003 | St. Goar et al. |
| 6,635,085 B1 | 10/2003 | Caffey et al. |
| 6,638,239 B1 | 10/2003 | Bergheim et al. |
| 6,652,578 B2 | 11/2003 | Bailey et al. |
| 6,666,841 B2 | 12/2003 | Gharib et al. |
| 6,666,885 B2 | 12/2003 | Moe |
| 6,666,886 B1 | 12/2003 | Tranquillo et al. |
| 6,669,725 B2 | 12/2003 | Scott |
| 6,673,109 B2 | 1/2004 | Cox |
| 6,676,698 B2 | 1/2004 | McGuckin, Jr. et al. |
| 6,676,702 B2 | 1/2004 | Mathis |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,692,512 B2 | 2/2004 | Jang |
| 6,695,866 B1 | 2/2004 | Kuehn et al. |
| 6,695,878 B2 | 2/2004 | McGuckin, Jr. et al. |
| 6,709,456 B2 | 3/2004 | Langberg et al. |
| 6,709,457 B1 | 3/2004 | Otte et al. |
| 6,716,241 B2 | 4/2004 | Wilder et al. |
| 6,716,244 B2 | 4/2004 | Klaco |
| 6,719,767 B1 | 4/2004 | Kimblad |
| 6,719,784 B2 | 4/2004 | Henderson |
| 6,719,786 B2 | 4/2004 | Ryan et al. |
| 6,719,787 B2 | 4/2004 | Cox |
| 6,719,788 B2 | 4/2004 | Cox |
| 6,719,789 B2 | 4/2004 | Cox |
| 6,719,790 B2 | 4/2004 | Brendzel et al. |
| 6,723,038 B1 | 4/2004 | Schroeder et al. |
| 6,723,122 B2 | 4/2004 | Yang et al. |
| 6,723,123 B1 | 4/2004 | Kazatchkov et al. |
| 6,726,715 B2 | 4/2004 | Sutherland |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,730,122 B1 | 5/2004 | Pan et al. |
| 6,736,791 B1 | 5/2004 | Tu et al. |
| 6,736,845 B2 | 5/2004 | Marquez et al. |
| 6,736,846 B2 | 5/2004 | Cox |
| 6,749,630 B2 | 6/2004 | McCarthy et al. |
| 6,752,813 B2 | 6/2004 | Goldfarb et al. |
| 6,752,828 B2 | 6/2004 | Thornton |
| 6,755,857 B2 | 6/2004 | Peterson et al. |
| 6,761,734 B2 | 7/2004 | Suhr |

(56) References Cited

U.S. PATENT DOCUMENTS

| | | |
|---|---|---|
| 6,761,735 B2 | 7/2004 | Eberhardt et al. |
| 6,764,494 B2 | 7/2004 | Menz et al. |
| 6,764,508 B1 | 7/2004 | Roehe et al. |
| 6,764,509 B2 | 7/2004 | Chinn et al. |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,770,083 B2 | 8/2004 | Seguin |
| 6,780,164 B2 | 8/2004 | Bergheim et al. |
| 6,780,200 B2 | 8/2004 | Jansen |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,231 B2 | 9/2004 | Liddicoat et al. |
| 6,793,673 B2 | 9/2004 | Kowalsky et al. |
| 6,797,000 B2 | 9/2004 | Simpson et al. |
| 6,797,001 B2 | 9/2004 | Mathis et al. |
| 6,797,002 B2 | 9/2004 | Spence et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,830,584 B1 | 12/2004 | Seguin |
| 6,830,585 B1 | 12/2004 | Artof et al. |
| 6,837,902 B2 | 1/2005 | Nguyen et al. |
| 6,840,246 B2 | 1/2005 | Downing |
| 6,840,957 B2 | 1/2005 | DiMatteo et al. |
| 6,846,324 B2 | 1/2005 | Stobie |
| 6,846,325 B2 | 1/2005 | Liddicoat |
| 6,858,039 B2 | 2/2005 | McCarthy |
| 6,860,895 B1 | 3/2005 | Akerfeldt et al. |
| 6,869,444 B2 | 3/2005 | Gabbay |
| 6,872,226 B2 | 3/2005 | Cali |
| 6,875,224 B2 | 4/2005 | Grimes |
| 6,875,230 B1 | 4/2005 | Morita et al. |
| 6,875,231 B2 | 4/2005 | Anduiza et al. |
| 6,881,199 B2 | 4/2005 | Wilk et al. |
| 6,881,224 B2 | 4/2005 | Kruse et al. |
| 6,883,522 B2 | 4/2005 | Spence et al. |
| 6,890,350 B1 | 5/2005 | Walak |
| 6,890,352 B1 | 5/2005 | Lentell |
| 6,890,353 B2 | 5/2005 | Cohn et al. |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,896,700 B2 | 5/2005 | Lu et al. |
| 6,902,576 B2 | 6/2005 | Drasler et al. |
| 6,908,478 B2 | 6/2005 | Alferness et al. |
| 6,908,481 B2 | 6/2005 | Cribier |
| 6,911,043 B2 | 6/2005 | Myers et al. |
| 6,913,608 B2 | 7/2005 | Liddicoat et al. |
| 6,916,338 B2 | 7/2005 | Speziali |
| 6,918,917 B1 | 7/2005 | Nguyen et al. |
| 6,921,407 B2 | 7/2005 | Nguyen et al. |
| 6,921,811 B2 | 7/2005 | Zamora et al. |
| 6,926,715 B1 | 8/2005 | Hauck et al. |
| 6,926,730 B1 | 8/2005 | Nguyen et al. |
| 6,929,653 B2 | 8/2005 | Strecter |
| 6,932,838 B2 | 8/2005 | Schwartz et al. |
| 6,936,067 B2 | 8/2005 | Buchanan |
| 6,939,359 B2 | 9/2005 | Tu et al. |
| 6,942,694 B2 | 9/2005 | Liddicoat et al. |
| 6,945,957 B2 | 9/2005 | Freyman |
| 6,945,978 B1 | 9/2005 | Hyde |
| 6,945,996 B2 | 9/2005 | Sedransk |
| 6,945,997 B2 | 9/2005 | Huynh et al. |
| 6,949,122 B2 | 9/2005 | Adams et al. |
| 6,951,571 B1 | 10/2005 | Srivastava |
| 6,951,573 B1 | 10/2005 | Dilling |
| 6,955,656 B2 | 10/2005 | Bergheim et al. |
| 6,955,689 B2 | 10/2005 | Ryan et al. |
| 6,958,076 B2 | 10/2005 | Acosta et al. |
| 6,962,605 B2 | 11/2005 | Cosgrove et al. |
| 6,964,682 B2 | 11/2005 | Nguyen-Thien-Nhon et al. |
| 6,964,683 B2 | 11/2005 | Kowalsky et al. |
| 6,964,684 B2 | 11/2005 | Ortiz et al. |
| 6,966,925 B2 | 11/2005 | Stobie |
| 6,966,926 B2 | 11/2005 | Mathis |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,995 B2 | 12/2005 | Mathis et al. |
| 6,979,350 B2 | 12/2005 | Moll et al. |
| 6,986,775 B2 | 1/2006 | Morales et al. |
| 6,989,027 B2 | 1/2006 | Allen et al. |
| 6,989,028 B2 | 1/2006 | Lashinski et al. |
| 6,997,950 B2 | 2/2006 | Chawla |
| 6,997,951 B2 | 2/2006 | Solem et al. |
| 7,001,411 B1 | 2/2006 | Dean |
| 7,004,176 B2 | 2/2006 | Lau |
| 7,007,396 B2 | 3/2006 | Rudko et al. |
| 7,007,698 B2 | 3/2006 | Thornton |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,018,407 B1 | 3/2006 | Wright et al. |
| 7,018,408 B2 | 3/2006 | Bailey et al. |
| 7,022,134 B1 | 4/2006 | Quijano et al. |
| 7,025,780 B2 | 4/2006 | Gabbay |
| 7,033,390 B2 | 4/2006 | Johnson et al. |
| 7,037,333 B2 | 5/2006 | Myers et al. |
| 7,037,334 B1 | 5/2006 | Hlavka et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,044,967 B1 | 5/2006 | Solem et al. |
| 7,048,754 B2 | 5/2006 | Martin et al. |
| 7,048,757 B2 | 5/2006 | Shaknovich |
| 7,052,487 B2 | 5/2006 | Cohn et al. |
| 7,052,507 B2 | 5/2006 | Wakuda et al. |
| 7,063,722 B2 | 6/2006 | Marquez |
| 7,066,954 B2 | 6/2006 | Ryan et al. |
| 7,070,616 B2 | 7/2006 | Majercak et al. |
| 7,077,862 B2 | 7/2006 | Vidlund et al. |
| 7,081,131 B2 | 7/2006 | Thornton |
| 7,087,064 B1 | 8/2006 | Hyde |
| 7,089,051 B2 | 8/2006 | Javerud et al. |
| 7,090,695 B2 | 8/2006 | Solem et al. |
| 7,101,396 B2 | 9/2006 | Artof et al. |
| 7,329,279 B2 | 2/2008 | Haug et al. |
| 7,331,991 B2 | 2/2008 | Kheradvar et al. |
| 7,470,285 B2 | 12/2008 | Nugent et al. |
| 7,967,853 B2 | 6/2011 | Eidenschink et al. |
| 8,070,800 B2 | 12/2011 | Lock et al. |
| 8,092,524 B2 | 1/2012 | Nugent et al. |
| 8,133,270 B2 | 3/2012 | Kheradvar et al. |
| 8,318,078 B2 | 11/2012 | Jagger et al. |
| 8,348,999 B2 | 1/2013 | Kheradvar et al. |
| 8,414,645 B2 | 4/2013 | Dwork et al. |
| 8,460,366 B2 | 6/2013 | Rowe |
| 8,740,976 B2 | 6/2014 | Tran et al. |
| 8,852,271 B2 | 10/2014 | Murray, III et al. |
| 8,870,949 B2 | 10/2014 | Rowe |
| 8,888,843 B2 | 11/2014 | Khairkhahan et al. |
| 8,956,404 B2 | 2/2015 | Börtlein et al. |
| 8,998,979 B2 | 4/2015 | Seguin et al. |
| 9,023,098 B2 | 5/2015 | Kuehn |
| 9,060,856 B2 | 6/2015 | Seguin et al. |
| 9,061,119 B2 | 6/2015 | Le et al. |
| 9,072,604 B1 | 7/2015 | Melnick et al. |
| 9,119,713 B2 | 9/2015 | Board et al. |
| 9,119,717 B2 | 9/2015 | Wang et al. |
| 9,132,008 B2 | 9/2015 | Dwork et al. |
| 9,295,547 B2 | 3/2016 | Costello et al. |
| 9,301,839 B2 | 4/2016 | Stante et al. |
| 9,333,077 B2 | 5/2016 | Peter |
| 9,358,108 B2 | 6/2016 | Börtlein et al. |
| 9,375,312 B2 | 6/2016 | Weber |
| 9,387,075 B2 | 7/2016 | Börtlein et al. |
| 2002/0026216 A1 | 2/2002 | Grimes |

(56) References Cited

U.S. PATENT DOCUMENTS

| | | |
|---|---|---|
| 2002/0151970 A1 | 10/2002 | Garrison et al. |
| 2002/0183835 A1 | 12/2002 | Taylor et al. |
| 2002/0183838 A1 | 12/2002 | Liddicoat et al. |
| 2003/0028247 A1 | 2/2003 | Cali |
| 2003/0040792 A1 | 2/2003 | Gabbay |
| 2003/0050694 A1 | 3/2003 | Yang et al. |
| 2003/0130729 A1 | 7/2003 | Paniagua et al. |
| 2003/0199975 A1 | 10/2003 | Gabbay |
| 2003/0229394 A1 | 12/2003 | Ogle et al. |
| 2003/0229395 A1 | 12/2003 | Cox |
| 2003/0236568 A1 | 12/2003 | Hojeibane et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015232 A1 | 1/2004 | Shu et al. |
| 2004/0015233 A1 | 1/2004 | Jansen |
| 2004/0019374 A1 | 1/2004 | Hojeibane et al. |
| 2004/0019377 A1 | 1/2004 | Taylor et al. |
| 2004/0019378 A1 | 1/2004 | Hlavka et al. |
| 2004/0024447 A1 | 2/2004 | Haverich |
| 2004/0024452 A1 | 2/2004 | Kruse et al. |
| 2004/0030321 A1 | 2/2004 | Fangrow, Jr. |
| 2004/0030381 A1 | 2/2004 | Shu |
| 2004/0030382 A1 | 2/2004 | St. Goar et al. |
| 2004/0030405 A1 | 2/2004 | Carpentier et al. |
| 2004/0034380 A1 | 2/2004 | Woolfson et al. |
| 2004/0039436 A1 | 2/2004 | Spenser et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0044403 A1 | 3/2004 | Bischoff et al. |
| 2004/0049207 A1 | 3/2004 | Goldfarb et al. |
| 2004/0049211 A1 | 3/2004 | Tremulis et al. |
| 2004/0059351 A1 | 3/2004 | Eigler et al. |
| 2004/0059411 A1 | 3/2004 | Strecker |
| 2004/0059412 A1 | 3/2004 | Lytle, IV et al. |
| 2004/0060161 A1 | 4/2004 | Leal et al. |
| 2004/0073301 A1 | 4/2004 | Donlon et al. |
| 2004/0073302 A1 | 4/2004 | Rourke et al. |
| 2004/0078072 A1 | 4/2004 | Tu et al. |
| 2004/0078074 A1 | 4/2004 | Anderson et al. |
| 2004/0082910 A1 | 4/2004 | Constantz et al. |
| 2004/0082923 A1 | 4/2004 | Field |
| 2004/0087975 A1 | 5/2004 | Lucatero et al. |
| 2004/0088045 A1 | 5/2004 | Cox |
| 2004/0092858 A1 | 5/2004 | Wilson et al. |
| 2004/0093070 A1 | 5/2004 | Hojeibane et al. |
| 2004/0093080 A1 | 5/2004 | Helmus et al. |
| 2004/0097979 A1 | 5/2004 | Svanidze et al. |
| 2004/0098098 A1 | 5/2004 | McGuckin, Jr. et al. |
| 2004/0102839 A1 | 5/2004 | Cohn et al. |
| 2004/0102840 A1 | 5/2004 | Solem et al. |
| 2004/0106991 A1 | 6/2004 | Hopkins et al. |
| 2004/0111096 A1 | 6/2004 | Tu et al. |
| 2004/0117009 A1 | 6/2004 | Cali et al. |
| 2004/0122448 A1 | 6/2004 | Levine |
| 2004/0122512 A1 | 6/2004 | Navia et al. |
| 2004/0122513 A1 | 6/2004 | Navia et al. |
| 2004/0122514 A1 | 6/2004 | Fogarty et al. |
| 2004/0122515 A1 | 6/2004 | Chu |
| 2004/0122516 A1 | 6/2004 | Fogarty et al. |
| 2004/0127979 A1 | 7/2004 | Wilson et al. |
| 2004/0127981 A1 | 7/2004 | Rahdert et al. |
| 2004/0127982 A1 | 7/2004 | Machold et al. |
| 2004/0133220 A1 | 7/2004 | Lashinski et al. |
| 2004/0133267 A1 | 7/2004 | Lane |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148018 A1 | 7/2004 | Carpentier et al. |
| 2004/0148019 A1 | 7/2004 | Vidlund et al. |
| 2004/0148020 A1 | 7/2004 | Vidlund et al. |
| 2004/0153147 A1 | 8/2004 | Mathis |
| 2004/0158321 A1 | 8/2004 | Reuter et al. |
| 2004/0162610 A1 | 8/2004 | Liska et al. |
| 2004/0167539 A1 | 8/2004 | Kuehn et al. |
| 2004/0172046 A1 | 9/2004 | Hlavka et al. |
| 2004/0176839 A1 | 9/2004 | Huynh et al. |
| 2004/0176840 A1 | 9/2004 | Langberg et al. |
| 2004/0181238 A1 | 9/2004 | Zarbatany et al. |
| 2004/0186444 A1 | 9/2004 | Daly et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0193191 A1 | 9/2004 | Starksen et al. |
| 2004/0193253 A1 | 9/2004 | Thorpe et al. |
| 2004/0193260 A1 | 9/2004 | Alferness et al. |
| 2004/0199155 A1 | 10/2004 | Mollenauer |
| 2004/0199183 A1 | 10/2004 | Oz et al. |
| 2004/0199191 A1 | 10/2004 | Schwartz |
| 2004/0204758 A1 | 10/2004 | Eberhardt et al. |
| 2004/0206363 A1 | 10/2004 | McCarthy et al. |
| 2004/0210240 A1 | 10/2004 | Saint |
| 2004/0210301 A1 | 10/2004 | Obermiller |
| 2004/0210304 A1 | 10/2004 | Seguin et al. |
| 2004/0210305 A1 | 10/2004 | Shu et al. |
| 2004/0210306 A1 | 10/2004 | Quijano et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0220654 A1 | 11/2004 | Mathis et al. |
| 2004/0220657 A1 | 11/2004 | Nieminen et al. |
| 2004/0225322 A1 | 11/2004 | Garrison et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225355 A1 | 11/2004 | Stevens |
| 2004/0225356 A1 | 11/2004 | Frater |
| 2004/0230117 A1 | 11/2004 | Tosaya et al. |
| 2004/0236411 A1 | 11/2004 | Sarac et al. |
| 2004/0236418 A1 | 11/2004 | Stevens |
| 2004/0236419 A1 | 11/2004 | Milo |
| 2004/0243153 A1 | 12/2004 | Liddicoat et al. |
| 2004/0243219 A1 | 12/2004 | Fischer et al. |
| 2004/0243227 A1 | 12/2004 | Starksen et al. |
| 2004/0243230 A1 | 12/2004 | Navia et al. |
| 2004/0254600 A1 | 12/2004 | Zarbatany et al. |
| 2004/0254636 A1 | 12/2004 | Flagle et al. |
| 2004/0260276 A1 | 12/2004 | Rudko et al. |
| 2004/0260317 A1 | 12/2004 | Bloom et al. |
| 2004/0260322 A1 | 12/2004 | Rudko et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0004583 A1 | 1/2005 | Oz et al. |
| 2005/0004667 A1 | 1/2005 | Swinford et al. |
| 2005/0004668 A1 | 1/2005 | Aklog et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021056 A1 | 1/2005 | St. Goar et al. |
| 2005/0021136 A1 | 1/2005 | Xie et al. |
| 2005/0027261 A1 | 2/2005 | Weaver et al. |
| 2005/0027348 A1 | 2/2005 | Case et al. |
| 2005/0027351 A1 | 2/2005 | Reuter et al. |
| 2005/0027353 A1 | 2/2005 | Alferness et al. |
| 2005/0033398 A1 | 2/2005 | Seguin |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0043792 A1 | 2/2005 | Solem et al. |
| 2005/0049679 A1 | 3/2005 | Taylor et al. |
| 2005/0049692 A1 | 3/2005 | Numamoto et al. |
| 2005/0049696 A1 | 3/2005 | Siess et al. |
| 2005/0049697 A1 | 3/2005 | Sievers |
| 2005/0054977 A1 | 3/2005 | Laird et al. |
| 2005/0055079 A1 | 3/2005 | Duran |
| 2005/0055087 A1 | 3/2005 | Starksen |
| 2005/0055088 A1 | 3/2005 | Liddicoat et al. |

(56) References Cited

U.S. PATENT DOCUMENTS

| | | |
|---|---|---|
| 2005/0055089 A1 | 3/2005 | Macoviak et al. |
| 2005/0060029 A1 | 3/2005 | Le et al. |
| 2005/0060030 A1 | 3/2005 | Lashinski et al. |
| 2005/0065460 A1 | 3/2005 | Laird |
| 2005/0065550 A1 | 3/2005 | Starksen et al. |
| 2005/0065594 A1 | 3/2005 | DiMatteo et al. |
| 2005/0065597 A1 | 3/2005 | Lansac |
| 2005/0070906 A1 | 3/2005 | Clark et al. |
| 2005/0070998 A1 | 3/2005 | Rourke et al. |
| 2005/0075584 A1 | 4/2005 | Cali |
| 2005/0075659 A1 | 4/2005 | Realyvasquez et al. |
| 2005/0075662 A1 | 4/2005 | Pedersen et al. |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075723 A1 | 4/2005 | Schroeder et al. |
| 2005/0075724 A1 | 4/2005 | Svanidze et al. |
| 2005/0075725 A1 | 4/2005 | Rowe |
| 2005/0075729 A1 | 4/2005 | Nguyen et al. |
| 2005/0075730 A1 | 4/2005 | Myers et al. |
| 2005/0080483 A1 | 4/2005 | Solem et al. |
| 2005/0085900 A1 | 4/2005 | Case et al. |
| 2005/0085904 A1 | 4/2005 | Lemmon |
| 2005/0090846 A1 | 4/2005 | Pedersen et al. |
| 2005/0096735 A1 | 5/2005 | Hojeibane et al. |
| 2005/0096738 A1 | 5/2005 | Cali et al. |
| 2005/0096739 A1 | 5/2005 | Cao |
| 2005/0096740 A1 | 5/2005 | Langberg et al. |
| 2005/0101975 A1 | 5/2005 | Nguyen et al. |
| 2005/0101988 A1 | 5/2005 | Stanford et al. |
| 2005/0102026 A1 | 5/2005 | Turner et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107872 A1 | 5/2005 | Mensah et al. |
| 2005/0113910 A1 | 5/2005 | Paniagua et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0131533 A1 | 6/2005 | Alfieri et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137676 A1 | 6/2005 | Richardson et al. |
| 2005/0137681 A1 | 6/2005 | Shoemaker et al. |
| 2005/0137682 A1 | 6/2005 | Justino |
| 2005/0137685 A1 | 6/2005 | Nieminen et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0143810 A1 | 6/2005 | Dauner et al. |
| 2005/0143811 A1 | 6/2005 | Realyvasquez |
| 2005/0149014 A1 | 7/2005 | Hauck et al. |
| 2005/0149179 A1 | 7/2005 | Mathis et al. |
| 2005/0149180 A1 | 7/2005 | Mathis et al. |
| 2005/0149181 A1 | 7/2005 | Eberhardt |
| 2005/0154442 A1 | 7/2005 | Eidenschink et al. |
| 2005/0159810 A1 | 7/2005 | Filsoufi |
| 2005/0159811 A1 | 7/2005 | Lane |
| 2005/0165477 A1 | 7/2005 | Anduiza et al. |
| 2005/0165478 A1 | 7/2005 | Song |
| 2005/0171472 A1 | 8/2005 | Lutter |
| 2005/0171601 A1 | 8/2005 | Cosgrove et al. |
| 2005/0177227 A1 | 8/2005 | Heim et al. |
| 2005/0177228 A1 | 8/2005 | Solem et al. |
| 2005/0182483 A1 | 8/2005 | Osborne et al. |
| 2005/0184122 A1 | 8/2005 | Hlavka et al. |
| 2005/0187614 A1 | 8/2005 | Agnew |
| 2005/0187616 A1 | 8/2005 | Realyvasquez |
| 2005/0187617 A1 | 8/2005 | Navia |
| 2005/0192606 A1 | 9/2005 | Paul, Jr. et al. |
| 2005/0192665 A1 | 9/2005 | Spenser et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222675 A1 | 10/2005 | Sauter |
| 2005/0222678 A1 | 10/2005 | Lashinski et al. |
| 2005/0228422 A1 | 10/2005 | Machold et al. |
| 2005/0228479 A1 | 10/2005 | Pavcnik et al. |
| 2005/0228486 A1 | 10/2005 | Case et al. |
| 2005/0228494 A1 | 10/2005 | Marquez |
| 2005/0228495 A1 | 10/2005 | Macoviak |
| 2005/0228496 A1 | 10/2005 | Mensah et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240202 A1 | 10/2005 | Shennib et al. |
| 2005/0240255 A1 | 10/2005 | Schaeffer |
| 2005/0240259 A1 | 10/2005 | Sisken et al. |
| 2005/0240262 A1 | 10/2005 | White |
| 2005/0244460 A1 | 11/2005 | Alferiev et al. |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mahis |
| 2005/0261759 A1 | 11/2005 | Lambrecht et al. |
| 2005/0267493 A1 | 12/2005 | Schreck et al. |
| 2005/0267560 A1 | 12/2005 | Bates |
| 2005/0267565 A1 | 12/2005 | Dave et al. |
| 2005/0267571 A1 | 12/2005 | Spence et al. |
| 2005/0267573 A9 | 12/2005 | Macoviak et al. |
| 2005/0267574 A1 | 12/2005 | Cohn et al. |
| 2005/0272969 A1 | 12/2005 | Alferness et al. |
| 2005/0273160 A1 | 12/2005 | Lashinski et al. |
| 2005/0278015 A1 | 12/2005 | Dave et al. |
| 2005/0283178 A1 | 12/2005 | Flagle et al. |
| 2005/0283231 A1 | 12/2005 | Haug et al. |
| 2005/0288779 A1 | 12/2005 | Shaoulian et al. |
| 2006/0000715 A1 | 1/2006 | Whitcher et al. |
| 2006/0004439 A1 | 1/2006 | Spenser et al. |
| 2006/0004442 A1 | 1/2006 | Spenser et al. |
| 2006/0009841 A1 | 1/2006 | McGuckin et al. |
| 2006/0009842 A1 | 1/2006 | Huynh et al. |
| 2006/0013805 A1 | 1/2006 | Hebbel et al. |
| 2006/0013855 A1 | 1/2006 | Carpenter et al. |
| 2006/0015136 A1 | 1/2006 | Besselink |
| 2006/0015178 A1 | 1/2006 | Moaddeb et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020332 A1 | 1/2006 | Lashinski et al. |
| 2006/0020334 A1 | 1/2006 | Lashinski et al. |
| 2006/0020335 A1 | 1/2006 | Kowalsky et al. |
| 2006/0020336 A1 | 1/2006 | Liddicoat |
| 2006/0025750 A1 | 2/2006 | Starksen et al. |
| 2006/0025784 A1 | 2/2006 | Starksen et al. |

(56) References Cited

U.S. PATENT DOCUMENTS

| | | |
|---|---|---|
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0025856 A1 | 2/2006 | Ryan et al. |
| 2006/0025857 A1 | 2/2006 | Bergheim et al. |
| 2006/0030747 A1 | 2/2006 | Kantrowitz et al. |
| 2006/0030866 A1 | 2/2006 | Schreck |
| 2006/0030882 A1 | 2/2006 | Adams et al. |
| 2006/0030885 A1 | 2/2006 | Hyde |
| 2006/0036317 A1 | 2/2006 | Vidlund et al. |
| 2006/0041305 A1 | 2/2006 | Lauterjung |
| 2006/0041306 A1 | 2/2006 | Vidlund et al. |
| 2006/0047297 A1 | 3/2006 | Case |
| 2006/0047338 A1 | 3/2006 | Jenson et al. |
| 2006/0047343 A1 | 3/2006 | Oviatt et al. |
| 2006/0052804 A1 | 3/2006 | Mialhe |
| 2006/0052867 A1 | 3/2006 | Revuelta et al. |
| 2006/0058817 A1 | 3/2006 | Starksen et al. |
| 2006/0058865 A1 | 3/2006 | Case et al. |
| 2006/0058871 A1 | 3/2006 | Zakay et al. |
| 2006/0058889 A1 | 3/2006 | Case et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0064174 A1 | 3/2006 | Zadno |
| 2006/0069400 A1 | 3/2006 | Burnett et al. |
| 2006/0069430 A9 | 3/2006 | Rahdert et al. |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse et al. |
| 2006/0095115 A1 | 5/2006 | Biadillah et al. |
| 2006/0095125 A1 | 5/2006 | Chinn et al. |
| 2006/0099326 A1 | 5/2006 | Keogh et al. |
| 2006/0100687 A1* | 5/2006 | Fahey ................. A61F 2/95 623/1.11 |
| 2006/0100697 A1 | 5/2006 | Casanova |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0106456 A9 | 5/2006 | Machold et al. |
| 2006/0111660 A1 | 5/2006 | Wolf et al. |
| 2006/0111773 A1 | 5/2006 | Rittgers et al. |
| 2006/0111774 A1 | 5/2006 | Samkov et al. |
| 2006/0116572 A1 | 6/2006 | Case |
| 2006/0116756 A1 | 6/2006 | Solem et al. |
| 2006/0122686 A1 | 6/2006 | Gilad et al. |
| 2006/0122692 A1 | 6/2006 | Gilad et al. |
| 2006/0122693 A1 | 6/2006 | Biadillah et al. |
| 2006/0127443 A1 | 6/2006 | Helmus |
| 2006/0129235 A1 | 6/2006 | Seguin et al. |
| 2006/0129236 A1 | 6/2006 | McCarthy |
| 2006/0135476 A1 | 6/2006 | Kutryk et al. |
| 2006/0135964 A1 | 6/2006 | Vesely |
| 2006/0135967 A1 | 6/2006 | Realyvasquez |
| 2006/0136044 A1 | 6/2006 | Osborne et al. |
| 2006/0136045 A1 | 6/2006 | Flagle et al. |
| 2006/0136052 A1 | 6/2006 | Vesely |
| 2006/0136054 A1 | 6/2006 | Berg et al. |
| 2006/0142848 A1 | 6/2006 | Gabbay |
| 2006/0149358 A1 | 7/2006 | Zilla et al. |
| 2006/0149360 A1 | 7/2006 | Schwammenthal et al. |
| 2006/0149367 A1 | 7/2006 | Sieracki |
| 2006/0149368 A1 | 7/2006 | Spence |
| 2006/0161248 A1 | 7/2006 | Case et al. |
| 2006/0161250 A1 | 7/2006 | Shaw |
| 2006/0167468 A1 | 7/2006 | Gabbay |
| 2006/0167541 A1 | 7/2006 | Lattouf |
| 2006/0167542 A1 | 7/2006 | Quintessenza |
| 2006/0167543 A1 | 7/2006 | Bailey et al. |
| 2006/0216173 A1 | 9/2006 | Kheradvar et al. |
| 2006/0235511 A1 | 10/2006 | Osborne |
| 2006/0282157 A1 | 12/2006 | Hill et al. |
| 2007/0112355 A1 | 5/2007 | Salahieh et al. |
| 2007/0168024 A1 | 7/2007 | Khairkhahan |
| 2007/0239255 A1 | 10/2007 | Hines |
| 2007/0255423 A1 | 11/2007 | Carpentier et al. |
| 2007/0282371 A1* | 12/2007 | Lee ................. A61B 17/29 606/205 |
| 2007/0293935 A1 | 12/2007 | Olsen et al. |
| 2007/0299499 A1 | 12/2007 | Hartley et al. |
| 2008/0029296 A1 | 2/2008 | Brist et al. |
| 2008/0039863 A1 | 2/2008 | Keegan et al. |
| 2008/0071364 A1 | 3/2008 | Kaye et al. |
| 2008/0161909 A1 | 7/2008 | Kheradvar et al. |
| 2008/0275550 A1 | 11/2008 | Kheradvar et al. |
| 2009/0030497 A1 | 1/2009 | Metcalf et al. |
| 2009/0082857 A1 | 3/2009 | Lashinski et al. |
| 2009/0099640 A1* | 4/2009 | Weng ................. A61F 2/95 623/1.11 |
| 2009/0192585 A1 | 7/2009 | Bloom et al. |
| 2010/0175693 A1 | 7/2010 | Wondka et al. |
| 2011/0040366 A1 | 2/2011 | Goetz et al. |
| 2011/0040374 A1 | 2/2011 | Goetz et al. |
| 2011/0112622 A1 | 5/2011 | Phan et al. |
| 2011/0196472 A1 | 8/2011 | Sugimoto et al. |
| 2011/0251664 A1 | 10/2011 | Acosta De Acevedo |
| 2013/0046373 A1 | 2/2013 | Cartledge et al. |
| 2013/0204356 A1 | 8/2013 | Dwork et al. |
| 2014/0100651 A1 | 4/2014 | Kheradvar et al. |
| 2014/0128963 A1 | 5/2014 | Quill et al. |
| 2014/0236292 A1 | 8/2014 | Braido |
| 2014/0296970 A1 | 10/2014 | Ekvall et al. |
| 2014/0296972 A1 | 10/2014 | Tegels et al. |
| 2015/0112430 A1 | 4/2015 | Creaven et al. |
| 2015/0196393 A1 | 7/2015 | Vidlund et al. |
| 2015/0257882 A1 | 9/2015 | Börtlein et al. |
| 2015/0272730 A1 | 10/2015 | Melnick et al. |
| 2015/0297346 A1 | 10/2015 | Duffy et al. |
| 2015/0327999 A1 | 11/2015 | Board et al. |
| 2016/0038281 A1 | 2/2016 | Delaloye et al. |
| 2016/0120643 A1 | 5/2016 | Kupumbati |
| 2016/0220363 A1 | 8/2016 | Peter |

FOREIGN PATENT DOCUMENTS

| | | |
|---|---|---|
| EP | 0466518 A2 | 1/1992 |
| EP | 0667133 B1 | 3/2001 |
| EP | 14763413.3 | 9/2016 |
| WO | WO 90/15582 A1 | 12/1990 |
| WO | WO 95/01669 A1 | 1/1995 |
| WO | WO 96/19159 A1 | 6/1996 |
| WO | WO 88/00459 A1 | 1/1998 |
| WO | WO 98/03656 A1 | 1/1998 |
| WO | WO 98/46115 A2 | 10/1998 |
| WO | WO 99/04724 A1 | 2/1999 |
| WO | WO 00/47139 A1 | 8/2000 |
| WO | WO 00/67679 A1 | 11/2000 |
| WO | WO 01/15650 A1 | 3/2001 |
| WO | WO 01/17462 A1 | 3/2001 |
| WO | WO 01/54624 A1 | 8/2001 |
| WO | WO 2004/043265 A2 | 5/2004 |
| WO | WO 2004/043273 A2 | 5/2004 |
| WO | WO 2004/043293 A2 | 5/2004 |
| WO | WO 2004/045378 A2 | 6/2004 |
| WO | WO 2004/062725 A1 | 7/2004 |
| WO | WO 2004/066803 A2 | 8/2004 |
| WO | WO 2004/066826 A2 | 8/2004 |
| WO | WO 2004/075789 A2 | 9/2004 |
| WO | WO 2004/082528 A2 | 9/2004 |
| WO | WO 2004/082536 A1 | 9/2004 |
| WO | WO 2004/082537 A1 | 9/2004 |
| WO | WO 2004/084746 A2 | 10/2004 |
| WO | WO 2004/084770 A1 | 10/2004 |
| WO | WO 2004/089250 A1 | 10/2004 |
| WO | WO 2004/089253 A1 | 10/2004 |
| WO | WO 2004/093638 A2 | 11/2004 |
| WO | WO 2004/103222 A1 | 12/2004 |
| WO | WO 2004/105584 A2 | 12/2004 |
| WO | WO 2004/112582 A2 | 12/2004 |
| WO | WO 2004/112585 A2 | 12/2004 |
| WO | WO 2004/112652 A2 | 12/2004 |
| WO | WO 2005/000152 A2 | 1/2005 |

(56) References Cited

FOREIGN PATENT DOCUMENTS

| | | |
|---|---|---|
| WO | WO 2005/002466 A2 | 1/2005 |
| WO | WO 2005/004753 A1 | 1/2005 |
| WO | WO 2005/007018 A2 | 1/2005 |
| WO | WO 2005/007036 A1 | 1/2005 |
| WO | WO 2005/007037 A1 | 1/2005 |
| WO | WO 2005/009285 A2 | 2/2005 |
| WO | WO 2005/011473 A2 | 2/2005 |
| WO | WO 2005/027790 A1 | 3/2005 |
| WO | WO 2005/027797 A1 | 3/2005 |
| WO | WO 2005/039428 A2 | 5/2005 |
| WO | WO 2005/039452 A1 | 5/2005 |
| WO | WO 2005/046488 A1 | 5/2005 |
| WO | WO 2005/046528 A1 | 5/2005 |
| WO | WO 2005/046530 A1 | 5/2005 |
| WO | WO 2005/055883 A1 | 6/2005 |
| WO | WO 2005/058206 A1 | 6/2005 |
| WO | WO 2005/070342 A1 | 8/2005 |
| WO | WO 2005/070343 A1 | 8/2005 |
| WO | WO 2005/072654 A1 | 8/2005 |
| WO | WO 2005/072655 A1 | 8/2005 |
| WO | WO 2005/079706 A1 | 9/2005 |
| WO | WO 2005/087139 A1 | 9/2005 |
| WO | WO 2005/087140 A1 | 9/2005 |
| WO | WO 2006/000763 A2 | 1/2006 |
| WO | WO 2006/002492 A1 | 1/2006 |
| WO | WO 2006/004679 A1 | 1/2006 |
| WO | WO 2006/011127 A2 | 2/2006 |
| WO | WO 2006/026912 A1 | 3/2006 |
| WO | WO 2006/027499 A2 | 3/2006 |
| WO | WO 2006/028821 A1 | 3/2006 |
| WO | WO 2006/034245 A2 | 3/2006 |
| WO | WO 2006/048664 A2 | 5/2006 |
| WO | WO 2006/050460 A1 | 5/2006 |
| WO | WO 2006/054107 A2 | 5/2006 |
| WO | WO 2006/054930 A1 | 5/2006 |
| WO | WO 2006/055982 A2 | 5/2006 |
| WO | WO 2006/063108 A1 | 6/2006 |
| WO | WO 2006/063181 A1 | 6/2006 |
| WO | WO 2006/063199 A2 | 6/2006 |
| WO | WO 2006/064490 A1 | 6/2006 |
| WO | WO 2006/065212 A1 | 6/2006 |
| WO | WO 2006/065930 A2 | 6/2006 |
| WO | WO 2006/066148 A2 | 6/2006 |
| WO | WO 2006/066150 A2 | 6/2006 |
| WO | WO 2006/069094 A1 | 6/2006 |
| WO | WO 2006/076890 A1 | 7/2006 |
| WO | PCT/US2006/07022 | 3/2008 |
| WO | PCT/US2008/000277 | 6/2008 |
| WO | PCT/US2008/001321 | 7/2008 |
| WO | PCT/US2006/07022 | 3/2009 |
| WO | PCT/US2008/000277 | 7/2009 |
| WO | PCT/US2008/001321 | 8/2009 |
| WO | PCT/US2012/049645 | 1/2013 |
| WO | WO 2013/022798 A1 | 2/2013 |
| WO | PCT/US2013/036469 | 7/2013 |
| WO | WO 2013/155474 A1 | 10/2013 |
| WO | PCT/US2012/049645 | 2/2014 |
| WO | PCT/US2014/028576 | 7/2014 |
| WO | PCT/US2014/028576 | 9/2015 |

OTHER PUBLICATIONS

Buzzatti, N., et al., "Computed tomography-based evaluation of aortic annulus, prosthesis size and impact on early residual aortic regurgitation after transcatheter aortic valve implantation", European Journal of Cardio-Thoracic Surgery, 2013, vol. 43, pp. 43-51.

Cribier, A., et al., "Percutaneous Transcatheter Implantation of an Aortic Valve Prosthesis for Calcific Aortic Stenosis: First Human Case Description", Circulation, 2002, vol. 106, pp. 3006-3008.

De Heer, L. M., et al., "Multimodality imaging throughout transcatheter aortic valve implantation", Future Cardiology, 2012, vol. 8, No. 3, pp. 413-424.

Dumont, E., et al., "Feasibility of transapical aortic valve implantation fully guided by transesophageal echocardiography", J. Thoracic and Cardiovasc. Surgery, 2009, vol. 138, pp. 1022-1024.

Elgort, D.R., et al., "Image-Guided and -Monitored Renal Artery Stenting Using Only MRI", J. Magn. Reson. Imaging, 2006, vol. 23, No. 5, pp. 619-627.

Falahatpisheh, A., et al., "High-speed particle image velocimetry to assess cardiac fluid dynamics in vitro: From performance to validation", European Journal of Mechanics—B/Fluids, 2012, vol. 35, pp. 2-8.

Ferrari, E., et al., "Imaging for trans-catheter pulmonary stent-valve implantation without angiography: role of intravascular ultrasound", European Journal of Cardio-thoracic Surgery, 2011, vol. 40, pp. 522-524.

Geisbüsch, S., et al., "Incidence and Management of CoreValve Dislocation During Transcatheter Aortic Valve Impiantation", Circ. Cardiovasc. Interv., 2010, vol. 3, pp. 531-536.

Giri, J., et al., "Procedural and Clinical Outcomes of the Valve-in-Valve Technique for Severe Aortic Insufficiency after Balloon-Expandable Transcatheter Aortic Valve Replacement", Catheterization and Cardiovascular Interventions, 2012, vol. 80, No. 1, pp. 139-147.

Groves, E. M., et al., "The Effects of Positioning of Transcatheter Aortic Valves on Fluid Dynamics of the Aortic Root", ASAIO Journal 2014, pp. 545-552.

Gurvitch, R., et al., "Transcatheter Valve-in-Valve Implantation for Failed Surgical Bioprosthetic Valves", J. Am. Coll. Cardiol., 2011, vol. 58, No. 21, pp. 2196-2209.

Jánosi, R. A., et al., "Guidance of percutaneous transcatheter aortic valve implantation by real-time three-dimensional transesophageal echocardiography—A single-center experience", Minimally Invasive Therapy & Allied Technologies, 2009, vol. 18, No. 3, pp. 142-148.

Kahlert, P., et al., "Towards real-time cardiovascular magnetic resonance guided transarterial CoreValve implantation: in vivo evaluation in swine", Journal of Cardiovascular Magnetic Resonance, 2012, vol. 14, No. 21, pp. 1-15.

Kapadia, S. R., et al., "Imaging for Transcatheter Valve Procedures", Current Problems in Cardiology, 2010, vol. 35, No. 5, pp. 228-276.

Kawase, Y., et al., "In Vivo Volumetric Analysis of Coronary Stent Using Optical Coherence Tomography with a Novel Balloon Occlusion-Flushing Catheter: A Comparison with Intravascular Ultrasound", Ultrasound in Medicine and Biology, 2005, vol. 31, No. 10, pp. 1343-1349.

Kempfert, J., et al., "Aortic annulus sizing: echocardiographic versus computed tomography derived measurements in comparison with direct surgical sizing", European Journal of Cardio-Thoracic Surgery, 2012, vol. 42, pp. 627-633.

Kheradvar, A., et al., "An In Vitro Study of Changing Profile Heights in Mitral Bioprostheses and their Influence on Flow", ASAIO Journal, 2006, vol. 52, pp. 34-38.

Kheradvar, A., et al., "Correlation Between Vortex Ring Formation and Mitral Annulus Dynamics During Ventricular Rapid Filling", ASAIO Journal, 2007, vol. 53, pp. 8-16.

Kheradvar, A., et al., "On Mitral Valve Dynamics and its Connection to Early Diastolic Flow", Ann. Biomed. Eng., 2009, vol. 37, No. 1, pp. 1-13.

Koos, R., et al., "Prevalence and Clinical Importance of Aortic Valve Calcification Detected Incidentally on CT Scans: Comparison with Echocardiography", Radiology, 2006, vol. 241, No. 1, pp. 76-82.

Kpodonu, J., et al., "Intravascular Ultrasound Imaging as Applied to the Aorta: A New Tool for the Cardiovascular Surgeon", Ann. Thorac. Surg., 2008, vol. 86, No. 4, pp. 1391-1398.

Leon, M. B., et al., "Transcatheter Aortic-Valve Implantation for Aortic Stenosis in Patients Who Cannot Undergo Surgery", The New England Journal of Medicine, 2010, vol. 363, No. 17, pp. 1597-1607.

Mack, M. J., et al., "Does Transcatheter Aortic Valve Implantation Mean the End of Surgical Aortic Valve Replacement?", Tex Heart Inst J., 2010, vol. 37, No. 6, pp. 658-659.

(56) References Cited

OTHER PUBLICATIONS

Makkar, R. R., et al., "Transcatheter Aortic-Valve Replacement for Inoperable Severe Aortic Stenosis", The New England Journal of Medicine, 2012, vol. 366, pp. 1696-1704.
Mintz, G. S., et al., "American College of Cardiology Clinical Expert Consensus Document on Standards for Acquisition, Measurement and Reporting of Intravascular Ultrasound Studies (IVUS)—A Report of the American College of Cardiology Task Force on Clinical Expert Consensus Documents", Journal of the American College of Cardiology, 2001, vol. 37, No. 5, pp. 1478-1492.
Moraveji, J., et al., "Computational Modeling of Nitinol Stents for Percutaneous Heart Valves", ASAIO Journal, ASAIO Cardiopulmonary Abstracts, 2010, vol. 56, No. 2, pp. 93.
Moss, R. R., et al., "Role of Echocardiography in Percutaneous Aortic Valve Implantation", JACC: Cardiovascular Imaging, 2008, vol. 1, No. 1, pp. 15-24.
Naqvi, T. Z., "Echocardiography in Percutaneous Valve Therapy", JACC: Cardiovascular Imaging, 2009, vol. 2, No. 10, pp. 1226-1237.
Piazza, N., et al., "Implantation of Two Self-Expanding Aortic Bioprosthetic Valves During the Same Procedure-Insights into Valve-in-Valve Implantation" ("Russian Doll Concept"), Catheterization and Cardiovascular Interventions, 2009, vol. 73, No. 4, pp. 530-539.
Rodés-Cabau, J., "Progress in Transcatheter Aortic Valve Implantation", Rev Esp Cardiol., 2010, vol. 63, No. 4, pp. 439-450.
Ruiz, C. E., et al., "First Percutaneous Transcatheter Aortic Valve-in-Valve Implant with Three Year Follow-Up", Catheterization and Cardiovascular Interventions, 2008, vol. 72, No. 2, pp. 143-148.
Sarkar, K., et al., "Core Valve Embolization: Technical Challenges and Management", Catheterization and Cardiovascular Interventions, 2012, vol. 79, No. 5, pp. 777-782.
Su, J. L., et al., "Photoacoustic imaging of coronary artery stents", Optics Express, 2009, vol. 17, No. 22, pp. 19894-19901.
Thielmann, M., et al., "Current developments in transcatheter aortic valve implantation techniques", Herz, 2011, vol. 36, No. 8, pp. 696-705.
Thomas, M., et al., "Thirty-Day Results of the SAPIEN Aortic Bioprosthesis European Outcome (SOURCE) Registry a European Registry of Transcatheter Aortic Valve Implantation Using the Edwards SAPIEN Valve", Circulation, 2010, vol. 122, pp. 62-69.
Treede, H., et al., "Six-month results of a repositionable and retrievable pericardial valve for transcatheter aortic valve replacement: The Direct Flow Medical aortic valve", J. Thoracic and Cardiovasc. Surg., 2010, vol. 140, No. 4, pp. 897-903.
Treede, H., et al., "Transapical transcatheter aortic valve implantation using the JenaValve™ system: acute and 30-day results of the multicentre CE-mark study", European Journal of Cardio-Thoracic Surgery, 2012, pp. 1-8.
Ussia, G. P., et al., "Management of Implant Failure During Transcatheter Aortic Valve Implantation", Catheterization and Cardiovascular Interventions, 2010, vol. 76, No. 3, pp. 440-449.
Ussia, G. P., et al., "The Valve-in-Valve Technique for Treatment of Aortic Bioprosthesis Malposition, An Analysis of Incidence and 1-Year Clinical Outcomes from the Italian CoreValve Registry", J. Am. Coll. of Cardiology, 2011, vol. 57, No. 9, pp. 1062-1068.
Webb, J. G., et al., "Transcatheter Valve-in-Valve Implantation for Failed Bioprosthetic Heart Valves", Circulation, 2010, vol. 121, pp. 1848-1857.

* cited by examiner

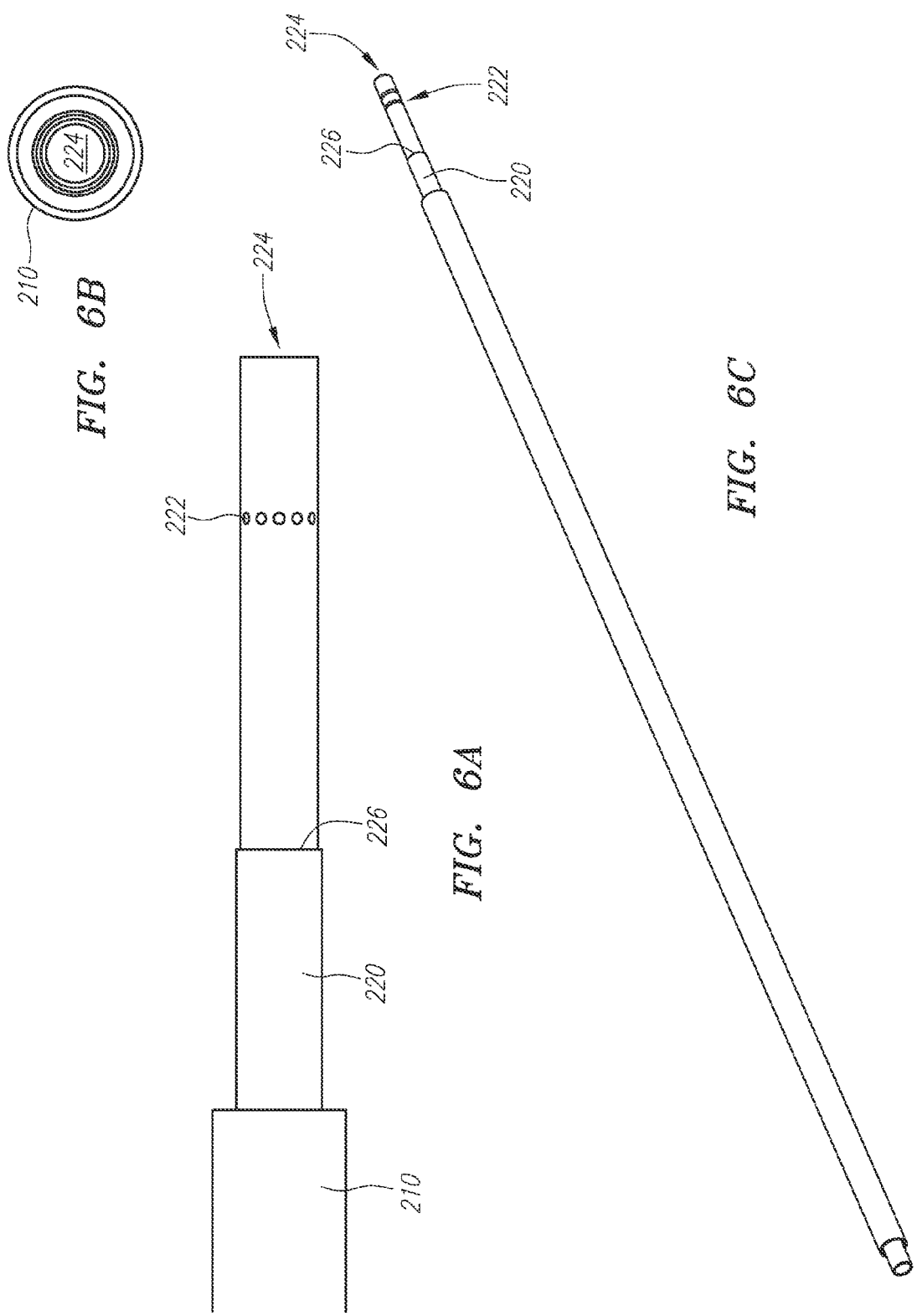

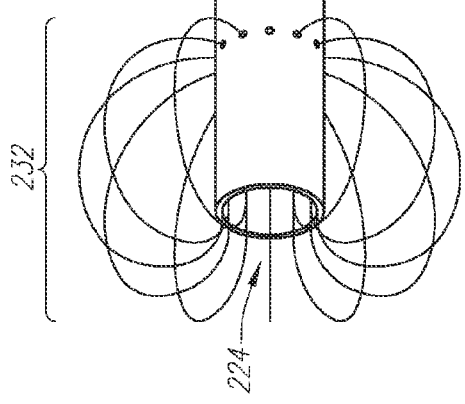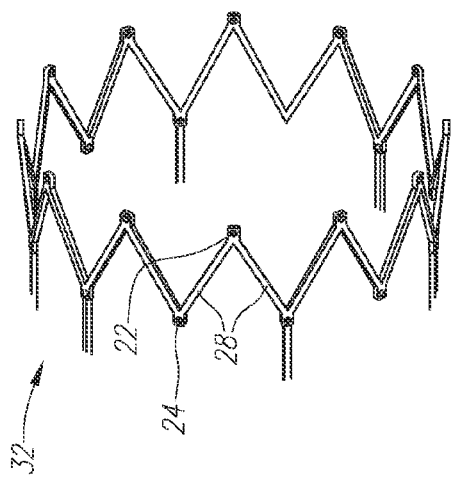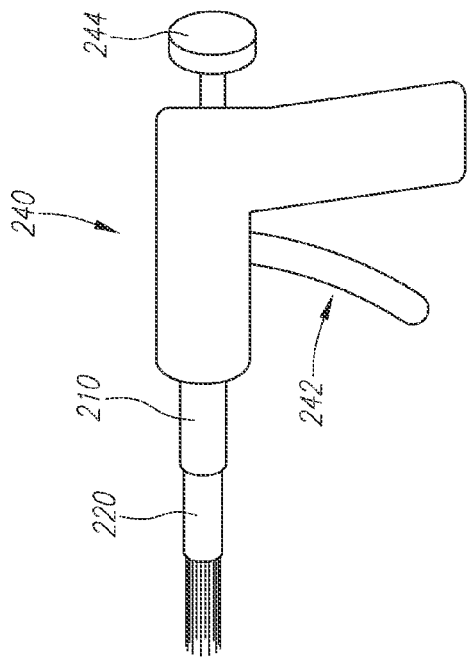
FIG. 8A
FIG. 8B
FIG. 9A

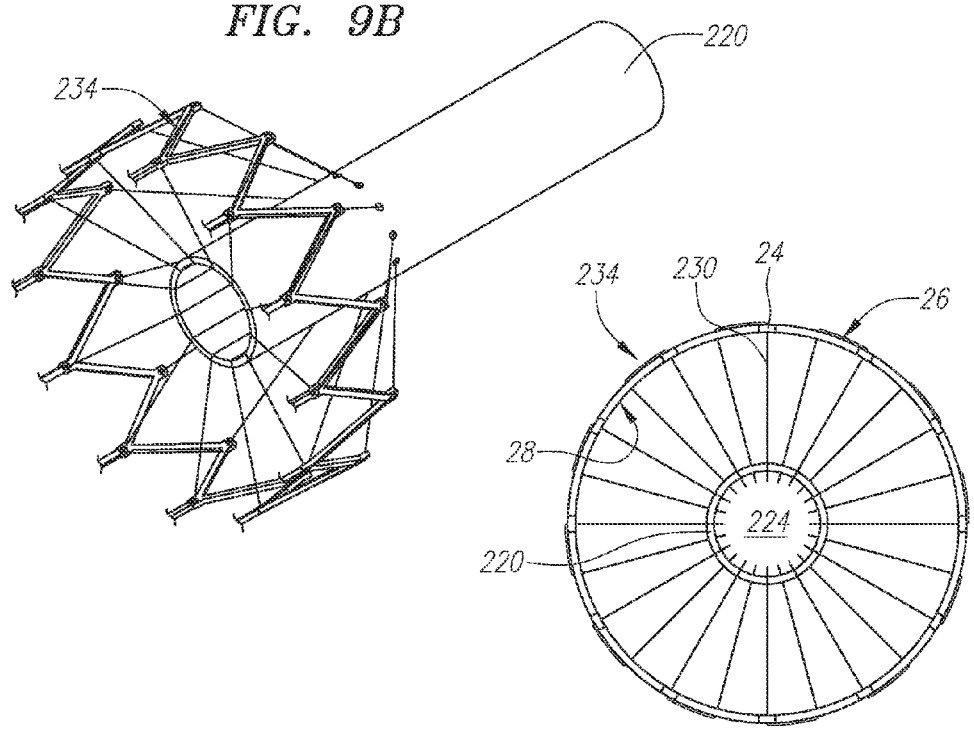
FIG. 9B
FIG. 9C
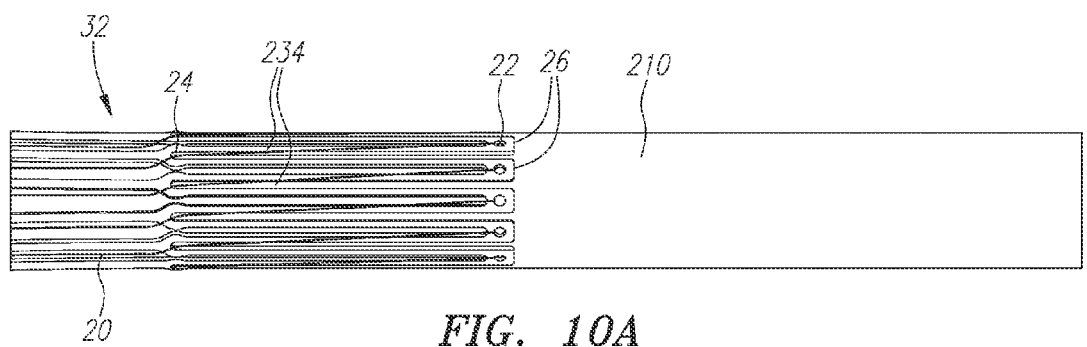
FIG. 10A
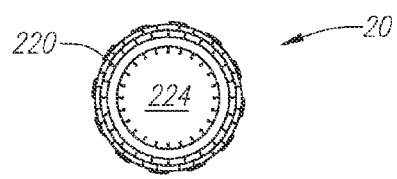
FIG. 10B

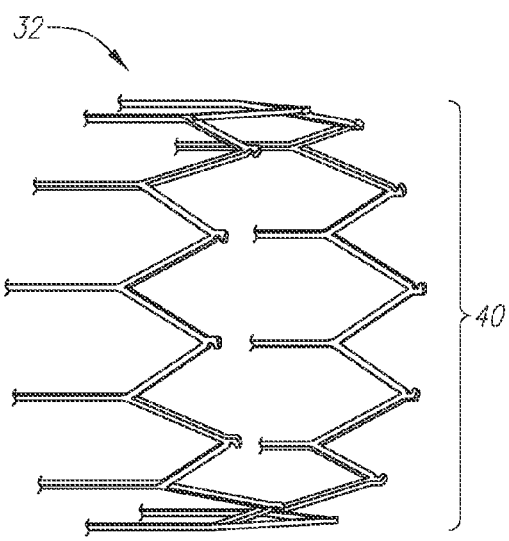
FIG. 11A
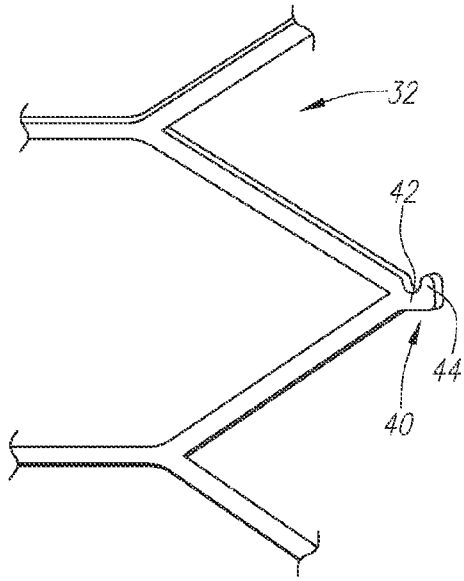
FIG. 11B
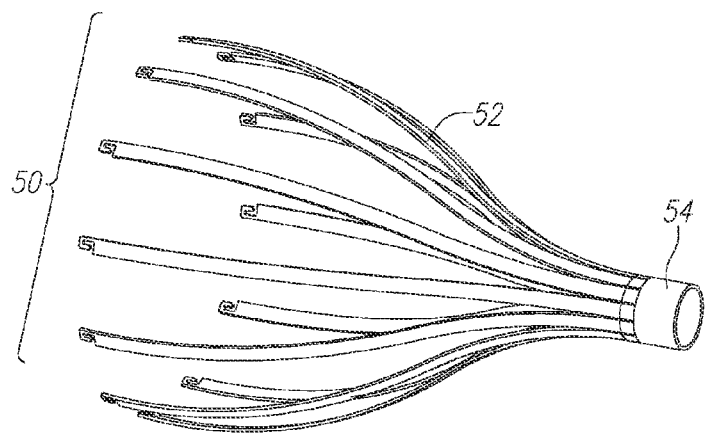
FIG. 12
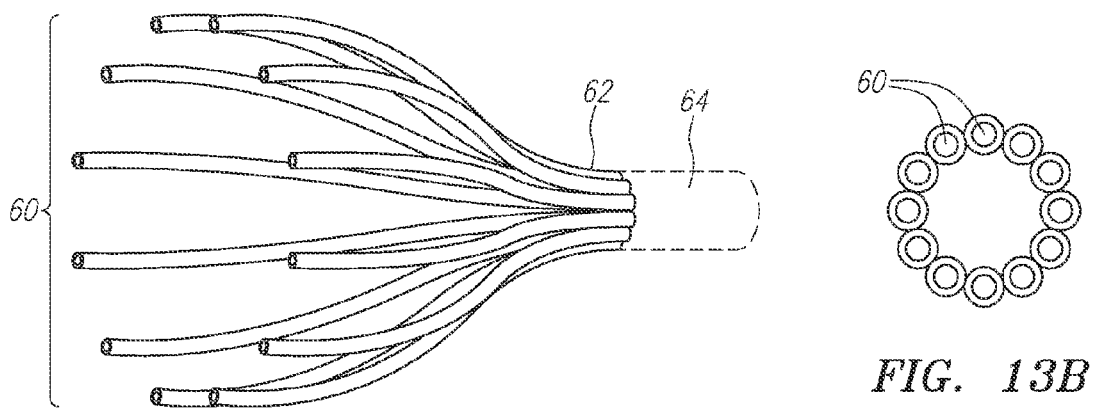
FIG. 13A
FIG. 13B

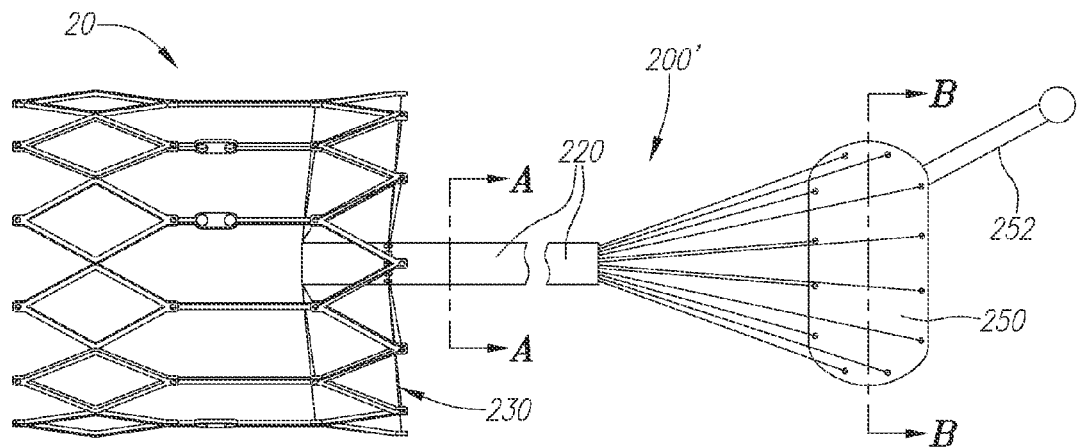
*FIG. 18A*
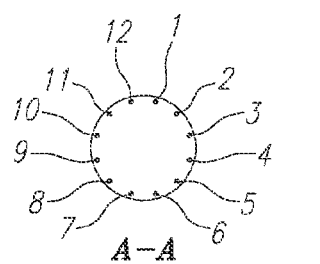
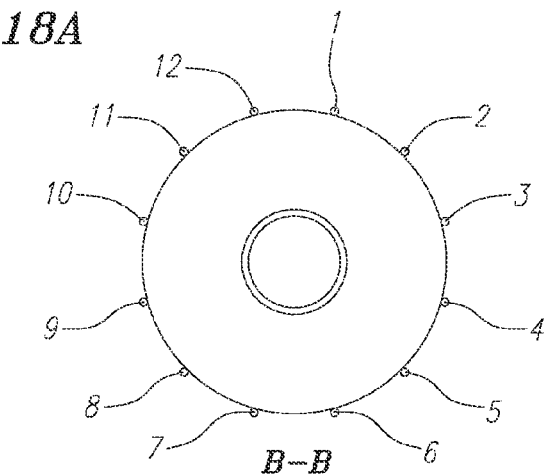
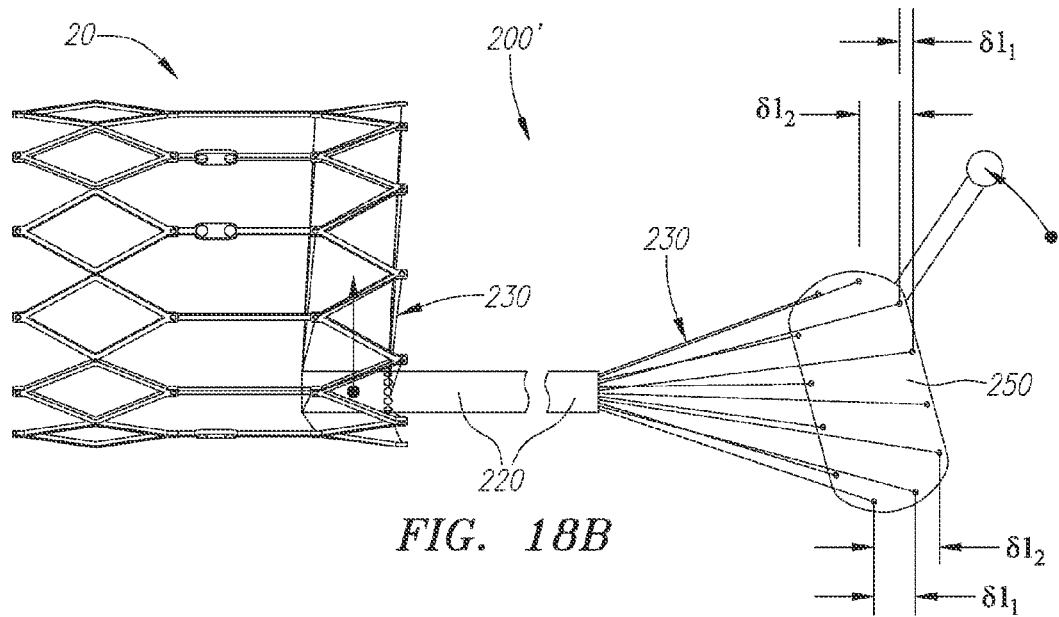
*FIG. 18B*

PERCUTANEOUS HEART VALVE DELIVERY SYSTEMS

RELATED APPLICATIONS

This filing claims the benefit of and priority to U.S. Provisional Patent Application No. 61/732,117 filed Nov. 30, 2012, U.S. Provisional Patent Application No. 61/682,663 filed Aug. 13, 2012, and U.S. Provisional Patent Application No. 61/623,410 filed Apr. 12, 2012. This filing is also a Continuation-in-Part of PCT/US12/49645 filed Aug. 3, 2012, which claims the benefit of U.S. Provisional Patent Application No. 61/515,679 filed Aug. 5, 2011 and U.S. Provisional Patent Application No. 61/666,657 filed Jun. 29, 2012. All preceding applications are incorporated by reference herein in their entireties for all purposes.

FIELD

The embodiments described herein relate to percutaneously-delivered heart valves and associated delivery systems.

BACKGROUND

Transcatheter aortic valve replacement (TAVR) procedures require image-guidance during implantation to successfully deploy the heart valve into the correct position within the patient's aortic annulus. Current image technology uses X-Ray, CT, MRI, or ultrasound to visualize the surrounding anatomy. However, only X-Ray can be used during the procedure for image guidance. X-Ray is not sufficient for visualization because it is a 2D projection of 3D anatomy that depends on the orientation angle of visualization. Currently, other imaging modalities can be used prior to the procedure and during follow-up, with the hopes that anatomical visualization can be directly correlated to the X-Ray images seen during the procedure. However, differences in contrast, resolution, and artifacts can produce differing results.

Correct valve positioning is crucial for treatment success and optimal outcomes after transcatheter valve implantation. For example, to maintain a stable and correct lengthwise position with respect to the aortic annulus, a stepwise deployment that allows the valve to be repositioned both circumferentially and in the axial direction (i.e., towards the left ventricle (LV) or the ascending aorta) is important.

However, most of the current technologies are limited by instant deployment, and once the valve is deployed, repositioning and/or percutaneous retrieval is not possible—or at least difficult or potentially problematic. Placement of the stented valve in a position that is too high (or proximal) can totally or partially obstruct the coronary ostia in a case of aortic implantation, which may result in myocardial infarction or ischemia. Additionally, if the valve is placed too high in the aorta, it may embolize into the aorta causing significant paravalvular regurgitation. On the other hand, implantation in a position that is too low (or distal) is accompanied by compression of the atrioventricular (AV) node in the membranous septum, which leads to conduction abnormalities.

Further technical developments with a focus on a positionable, repositionable, and/or percutaneously retrievable valve design allow optimal placement and may thereby significantly reduce the risk of paravalvular aortic regurgitation, myocardial infarction, or ischemia related to improper positioning. Likewise, advances in imaging to facilitate optimal heart valve placement are needed.

SUMMARY

The embodiments described herein address the need for improved catheter devices for coordinated delivery, positioning, repositioning and/or percutaneous retrieval of the percutaneously implanted heart valves. The delivery system apparatus is a tool that may incorporate a guide wire lumen. As such, a given device may be suitable for so-called "over-the-wire" use and include a delivery sheath covering that restrains the stent frame of the valve. Alternatively, the delivery device may be tracked trough a catheter serving such function, as in a so-called "guide" or "delivery" catheter.

In one embodiment, the delivery apparatus includes a number of arms (such as, but not limited to three) embedded within its body that hold the valve's stent during the delivery procedure when it is in the collapsed state. The arms are equipped with adjustable springs that are remotely controllable by the operator, and allow for robust radial expansion or deployment of the collapsed stent in increments.

In use, the arms remain attached to the valve stent frame until the stent frame is fully deployed. If the stent/stent frame is not properly deployed, the arms, which are still releasably attached to the stent until intended release, can be used for partial contraction of the stent for repositioning purposes. When the stented valve is properly positioned as desired within the heart, the arms will be released from the stent, and return to their embedded/retracted positions within the apparatus. Then the entire apparatus is retracted. It may be retracted from the heart or vasculature over any guide wire used and/or through any delivery catheter employed for site access.

In another system embodiment allowing for stented valve delivery, repositioning, and/or percutaneous retrieval, draw line filaments are positioned through the distal end of a pusher sleeve (or draw tube), along a lumen of the sleeve (or tube), out through holes in the sleeve (or tube), out through proximal frame holes, along the surface of a heart valve frame, in through distal frame holes, in through the distal end of the sleeve (or tube), along the lumen of the sleeve (or tube), and out the proximal end of the sleeve (or tube). Variations on this approach are possible as are various optional features of the stent frame facilitating such use.

The draw lines may comprise polyester (PE), PTFE, suture material, or another high strength (and preferably biocompatible fiber) braid or bundle of fibers such as ultra-high-molecular-weight polyethylene (UHMWPE, sometimes shortened to UHMW). In this embodiment and others described herein, the heart valve frame may comprise superelastic NiTi alloy heatset in a desired shape, it may be constructed of a so-called "engineering plastic" such as polyetheretherketone (PEEK) or may be constructed otherwise. Various surface treatments or finishes may be desirable. In the case of a NiTi (Nitinol) or another metallic material implant, an electro-polished surface may be preferred.

Collapsed and expanded states of a heart valve can be controlled by varying the position and/or tension applied to the draw lines. A customized handle may be provided for user interface. Draw line tension can be increased until the heart valve frame is fully collapsed and fully releasing the draw line tension allows the self-expanding heart valve frame to fully expand. The heart valve frame may be put in an intermediate state by varying the tension applied to the draw lines. Moreover, the system can be setup to allow a range of lateral control of the stent position during delivery. In one variation, a "joystick" control interface is provided; in another a model of the implant (or at least the stent frame portion of the valve to be delivered) is used.

In yet another delivery system embodiment allowing for delivery, repositioning, and/or percutaneous retrieval, different means or entities are provided to control the state of device deployment (variably, from fully collapsed to fully expanded) of the proximal end of a self-expanding heart valve device. Such means or entities pertain to the use of multiple sleeve or sheath features (herein optimally referred to as "zip tube" parts or an assembly with "zip tube" sheaths or fingers) provided to mechanically change an angle between adjacent strut elements and thereby the proximity of the struts. In use, the zip tube sheaths (or fingers) collapse the heart valve frame by "zipping" the struts into closer proximity.

In this embodiment, the ends of a self-expanding heart valve frame are configured with a link feature. A self-expanding retainer is constructed and configured with diametrically collapsible retainer arms or fingers. A zip tube part or assembly with diametrically expandable/collapsible sheath fingers is configured in such a manner to allow the zip tube fingers to slide over the retainer fingers. The ends of the retainer fingers are configured with a clasp or link feature so as to mate to the heart valve frame clasp or link features.

The zip tube assembly may be partially advanced (distally) to trap the heart valve frame and retainer such that they will not unlink because the inner diameter (or inner dimension(s)) of the zip tube fingers are constructed so as to constrain the linked heart valve frame and retainer from unlinking when positioned around the linked frame or retainer. With the retainer serving as a means to secure the valve in position, the zip tube assembly may be variably advanced (relative to the linked heart valve frame or retainer) to variably (e.g., partially) collapse the proximal end of the heart valve device or fully advanced to fully collapse the proximal end of the heart valve device.

The zip tube part assembly may be variably retracted to allow the proximal end of the self-expanding heart valve device to variably (partially) expand or retracted sufficient to allow the self-expanding heart valve device to fully expand. Alternatively, the zip part or assembly may be secured in position and the retainer may be variably retracted to variably collapse the proximal end of the heart valve device up to fully collapsed or variably advanced to allow the self-expanding heart valve device to variably expand up to fully expanded. The zip tube part or assembly can be fully retracted allowing the heart valve frame and retainer to unlink thereby releasing the heart valve device from the delivery system so that the heart valve device may be left in position and the delivery system may be removed.

In addition, any of the subject delivery system architectures may incorporate a visualization system for image-directed heart valve delivery. Alternatively, other features for restraining and/or manipulating a self-expanding stent frame or a ballooned stent frame approach may be employed in an image-guided system. All of these embodiments involve a catheter or catheter-like device that utilizes an integrated imaging modality with a deployment mechanism. As such, these embodiments may be used to accurately deploy a heart valve into a patient with greater accuracy and precision than with current procedural imaging modalities where direct visual confirmation is not possible.

In these embodiments, the delivery system incorporates a catheter-based imaging modality within the device, such as, but not limited to, intravascular ultrasound (IVUS), intravascular photoacoustic (IVPA) imaging, optical coherence tomography (OCT), raman spectroscopy, or an optical method, capable of detecting features of a vessel in which the catheter is inserted. The selected imaging systems allow clinicians to image both the surrounding anatomy and the advancing catheter in real-time during the procedure.

In one example, since IVUS is a tomographic imaging modality, a 3D image of the aortic root can be produced through pull-back imaging. High-resolution IVUS is well-known for interrogating the lumen wall of vessels and has also been used to visualize metal stents in vivo. In the example of IVUS hardware, a physician can accurately image and position the implantable valve device without the use of ionizing radiation or nephrotoxic contrast agents. Furthermore, IVUS advantageously provides for a real-time imaging modality.

A catheter system can be based upon an imaging catheter or a valve delivery catheter. In an embodiment where the catheter system is based upon the valve delivery catheter, the imaging modality device can be inserted through the center of the valve delivery catheter, where the active imaging element is aligned with a feature of the valve delivery catheter, such as, but not limited to the catheter tip, the distal or proximal end of the valve stent, or some other predetermined landmark of the valve delivery catheter. Positioning of the imaging device on the circumference of the valve delivery catheter is also possible in another embodiment to prevent visual hindrance from the implanted stent.

In yet another embodiment, the valve delivery system is based upon the imaging catheter, and the deployment mechanism is inserted through the lumen of the imaging catheter, such as, but not limited to, through a guidewire port of the imaging catheter. Furthermore, the delivery system referred herein is not limited to the delivery of a heart valve device, but could be used to deliver therapy to a localized region through the use of a catheter. Such examples of delivery could include, but are not limited to, delivery of drugs or other therapeutic agents, delivery of RF irradiation, or delivery of another device.

Operation of the delivery system allows visualization of the surrounding anatomy during insertion of the imaging catheter in the context of the location of the delivery catheter. As such, the location of the delivery catheter relative to the surrounding environment may always be known. In one embodiment, the delivery system is fixed relative to the imaging transducer within the catheter. In another embodiment, the two components can be moved relative to one another. However, in embodiments where relative motion is allowed, the relative motion is advantageously tracked or known in order to maintain accuracy in the advancing catheter.

The subject delivery devices, kits in which they are included (with and without valve installation or assembly), methods of use and manufacture (such as assembly of the delivery system and frame alone and/or with included valve) are all included within the scope of the present disclosure. Some aspects of the same are described above; more detailed discussion is presented in connection with the figures below.

Other systems, devices, methods, features, and/or advantages of the subject matter described herein will be or will become apparent to one with skill in the art upon examination of the following figures and detailed description. It is intended that all such additional systems, devices, methods, features, and/or advantages be included within this description and be within the scope of the subject matter described herein, regardless of whether recited in this summary section. In no way should the features of the example embodiments in this or any other section be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely. Variations other than those shown in the figures are contemplated as described in a broader sense in the above summary section, as generically claimed, or otherwise.

FIGS. 6A-6C illustrate side, end, and perspective views, respectively, of the delivery device sleeve of the second embodiment.

FIG. 8A illustrates a variation of the subject stent frame and FIG. 8B illustrates a variation of the subject delivery sleeve with associated draw line filaments.

FIGS. 9A-9C are side, perspective, and end views, respectively, illustrating the components in FIGS. 8A and 8B assembled together.

FIGS. 10A and 10B are side and end views, respectively, illustrating the same assembled components shown in a compressed state.

FIGS. 11A and 11B are partial perspective and detail side views, respectively, illustrating a stent frame for a third embodiment.

FIG. 12 is a perspective view illustrating a frame retainer with retainer fingers.

FIGS. 13A and 13B are perspective and end views, respectively, illustrating a zip tube part or assembly and zip tube fingers.

FIGS. 18A and 18B are side views illustrating the stent frame embodiment of FIG. 17 associated with a delivery device, with the stent frame in a neutral and a laterally displaced position, respectively.

DETAILED DESCRIPTION

Various example embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act, or step to the objective(s), spirit, or scope of the present inventive subject matter. All such modifications are intended to be within the scope of the claims made herein.

FIGS. 1A-1F illustrate an implant 2 and a suitable approach to valve 10 attachment and its manipulation for delivery in coordinated use with an expandable stent frame 20. Further details as to valve construction and/or its manipulation for delivery may be appreciated in review of U.S. Pat. No. 8,133,270 to Kheradvar, et al., incorporated by reference herein in its entirety for all purposes. Features of the stent frame elaborated upon below in the various embodiments may be added to those shown in FIGS. 1A-1F or used in connection with other suitable stent frame and/or other valve architectures.

Figure 1A:
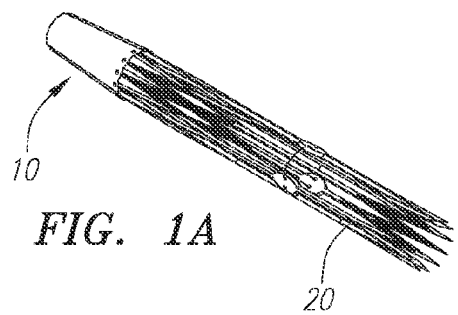
FIGS. 1A-1F are perspective views illustrating an example embodiment of a stent frame and valve in various stages of deployment as may be employed in connection with the embodiments herein.
Figure 1B:
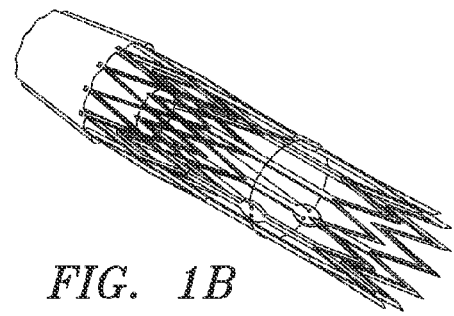
Figure 1C:
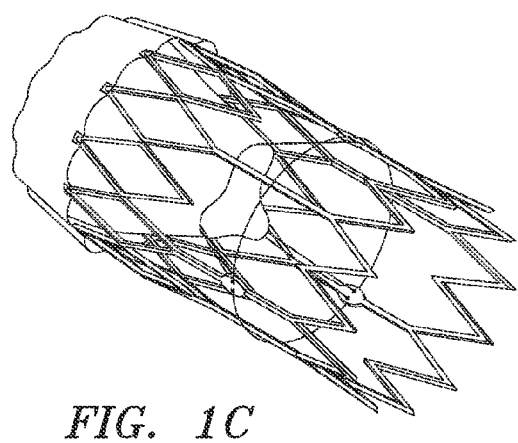
Figure 1D:
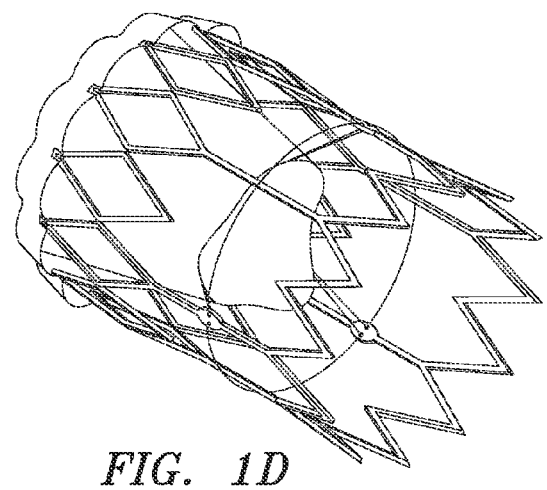
Figure 1E:
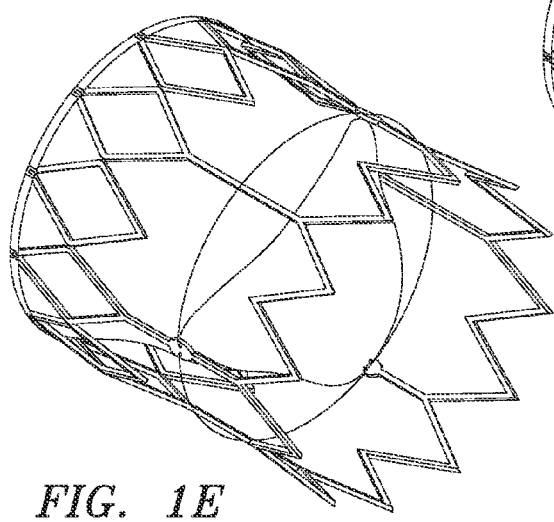
Figure 1F:
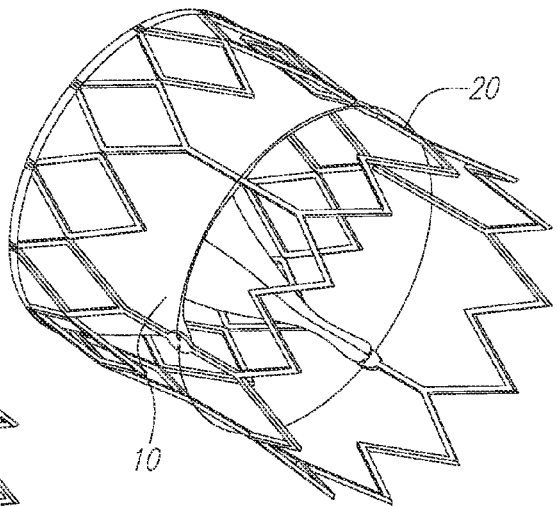
Figure 2A:
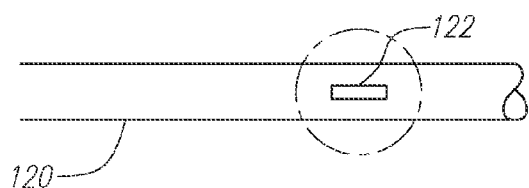
FIG. 2A is a detail view illustrating the delivery device sleeve of a first embodiment showing the location of one of a plurality of embedded arms.
Figure 2B:
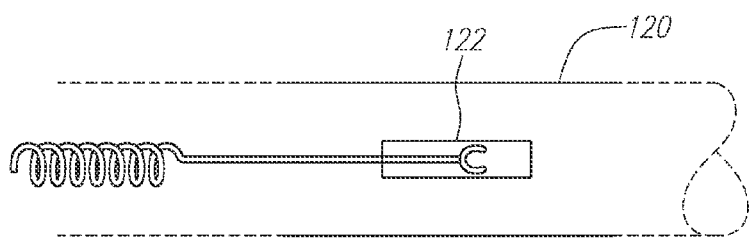
FIG. 2B is a detail view illustrating the arm at the location in FIG. 2A connected to a spring system for controlling stent frame deployment.
Figure 3:
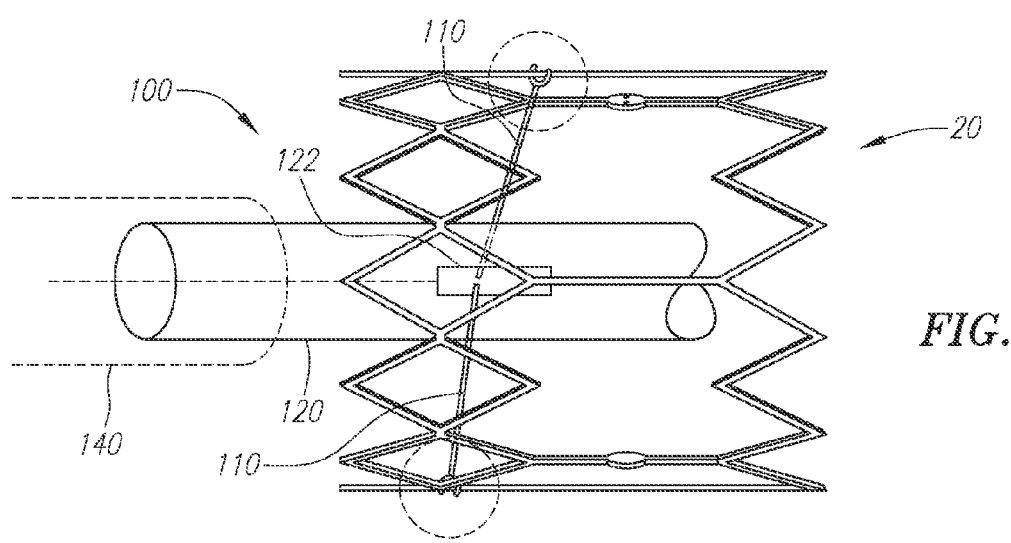
FIG. 3 is a system overview illustrating the arms releasably attached to a stent frame.

In any case, implant 2 (e.g., valve 10 and stent frame 20) is directly applicable for coordinated use with a delivery system as shown in FIGS. 2A-4B. More specifically, a delivery system apparatus for controlled deployment of a stented heart valve system in increments is shown. The system provides for repositioning a stented heart valve system during and after deployment. As variously illustrated, device 100 includes a plurality of deployable arms 110. These are adjustably deployable. The arms are first embedded inside the apparatus. FIG. 2B illustrates the location of one of the embedded arms 110 within a delivery device sleeve 120. For tracking to the target site, the arms are hidden. The arms exit the sleeve through ports or slots 122 in the wall of the sleeve. The arm lengths are adjustable and the arms are releasably attached to the stent of the stented valve. As shown in FIG. 2B, each arm may be equipped with an in-line adjustable spring that is controllable by the operator remotely. As illustrated in FIG. 3, such actuation allows for robust radial expansion or deployment of the collapsed stent frame in increments.

The arms remain attached to the stent until the stent is fully deployed. During tracking to a site for deployment, the stented valve may be covered by a sheath incorporated in the delivery system or pass within a delivery catheter (either case illustrated by an optional sleeve 140). If the stent is not properly deployed, the arms, which are still releasably attached to the stent, can be used for partial contraction of the stent for repositioning purposes. When the stented valve is properly positioned within the heart, the arms will be released from the stent, and return to their embedded positions within the apparatus. Then the apparatus will be retracted into the sheath or through the delivery catheter from the heart or vasculature.

Figure 4A:
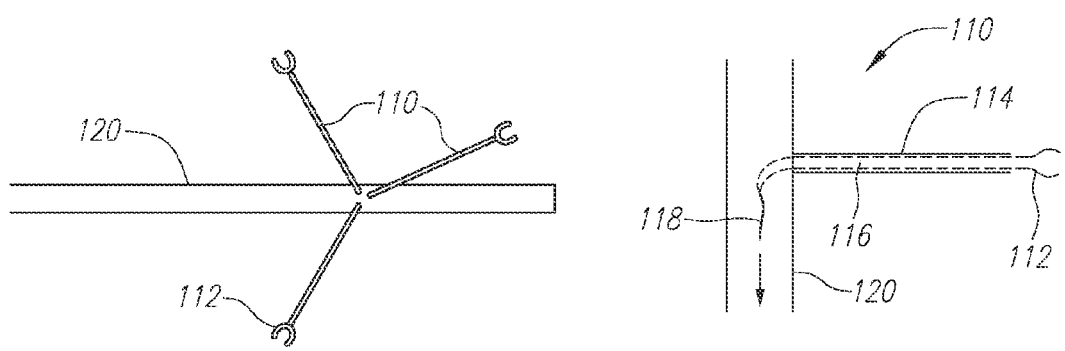
FIG. 4A is a detail view illustrating the arms fully extended from the delivery apparatus and FIG. 4B is a detail view illustrating a hollow deployment arm with strings inside and a pull/push mechanism inside the guide tube or sleeve.
Figure 4B:
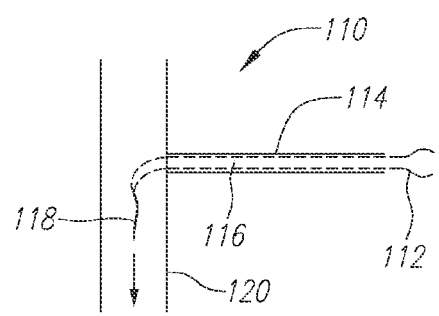

As seen in FIG. 4A in which the stent frame is detached, each arm may terminate in a releasable hook, jaw, clevis 112 or the like for such purpose(s). The connection and release may be provided by a simple snap fit. Otherwise it may be provided by a more active means for stent frame interface as illustrated in FIG. 4B, that shows an arm comprising a hollow micro tube or sheath 114 with spring loaded strings or filaments 116 inside where a string or filament 118 inside the guide tube or sleeve 120 can be used to control the closing and opening of the hooks 112.

FIGS. 5A-5E illustrate progressive stages of implant deployment and recapture for a second embodiment. Here, in a system pictured for over-the-wire tracking to its deployment site, a delivery system 200 includes a sheath 210 (with distal radiopaque marker 212) coaxial with a pusher sleeve 220. A distal portion of sleeve 220 includes apertures 222 through which filaments 230 pass into and proximally within the length of the sleeve. The filaments loop from these apertures through proximal stent frame apertures 22 and more distal stent frame apertures 24 (or alternatively past strut junctions in a different stent configuration) and into a distal end 224 of the sleeve (or a second set of distal apertures (not shown) in the sleeve if so-desired). Such details of the sleeve are shown unobscured in FIGS. 6A-6C, as is an optional shoulder 226 for abutting proximal end or crown sections 26 of the stent frame and guide sheath 210 of the proximal end or crowns of the stent frame.

Figure 7A:
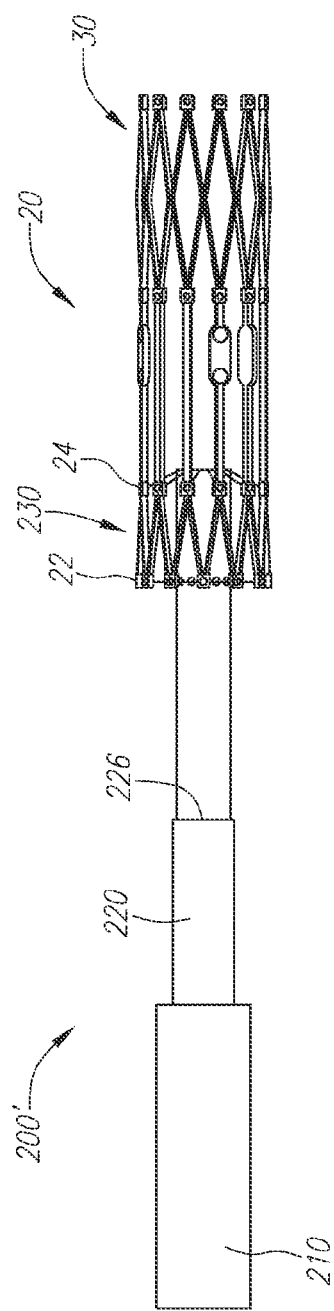
FIGS. 7A and 7B are side views illustrating the sent frame associated with the delivery device sleeve in contracted and expanded states, respectively.
Figure 7B:
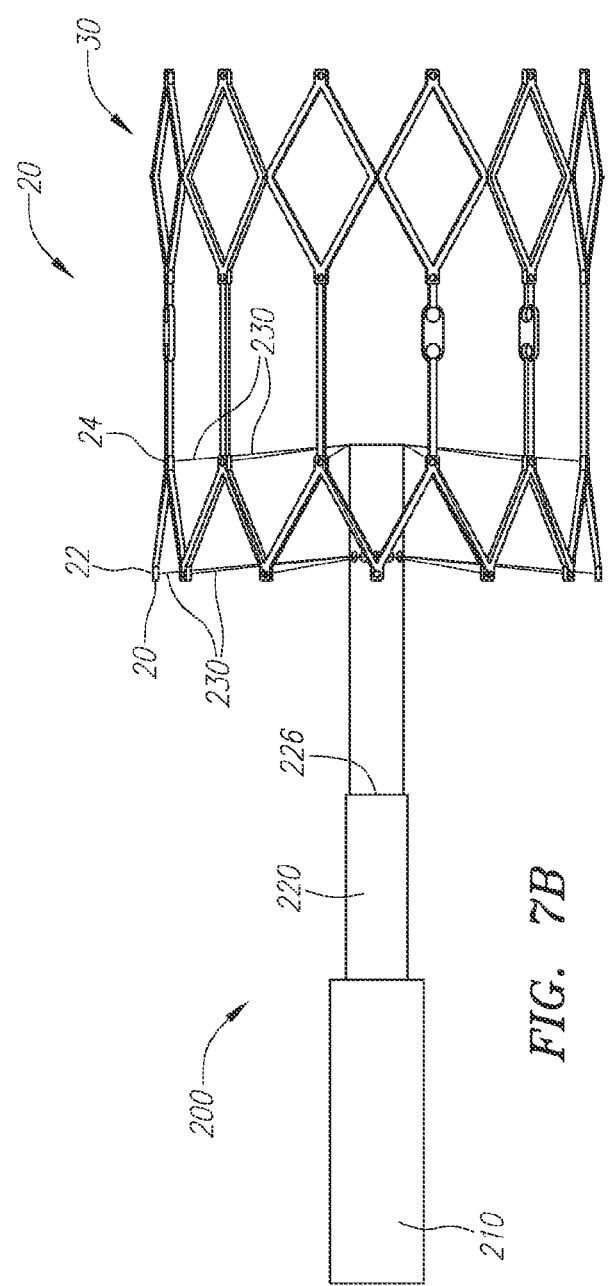

Regarding interaction between the stent frame and delivery system 200, FIGS. 7A and 7B provide side views of the stent frame associated with the delivery device sleeve in contracted and expanded states, respectively. Here, the manner of stent frame expansion and contraction as related to extended filament 230 length is clearly visible.

FIGS. 8A and 8B further illustrate such details as described above. When assembled in a delivery system 200, stent frame 20 will be captured within loops 232. The assembled relation of elements is shown in each of FIGS. 9A-9C and FIGS. 10A and 10B. Comparing FIGS. 9A-9C to FIGS. 10A and 10B, the state of the stent frame is changed from open or expanded in the former trio of figures, to compressed in the latter pair.

Such control is achievable by remote actuation of the loop filaments with a customized handle or other user interface means. Any handle may include means for group control of the filaments and independent control of sheath position. Such a handle 240 may include separate "grip" 242 and "plunger" or "slide" 244 interfaces as illustrated by example in FIG. 9A for such purposes. Otherwise, mechanism internal to the handle can automate all of the various control procedure(s) by actuating a grip 242, alone.

FIGS. 9A and 9B also offer good illustration of the manner in which filaments 230 pass through apertures 22, 24 and run along interposed strut sections 28. FIG. 9C illustrates the radial relationship of the apertures and filament 230 portions. Here, a crossing segment 234 of the filament between the apertures 22 and 24 is positioned outside of and opposing strut section 28. The crossing segments are angled with the struts when the stent frame is in an expanded state and more close to axially aligned when the stent is compressed as shown in FIGS. 10A and 10B.

As noted above, the transition between the open and compressed states (and states therebetween) is managed by letting-out or reeling-in the draw line filament determining the size of the control loop. Ultimately, one end of the line is pulled all of the way through the stent aperture to finally release the implant.

Figure 5A:
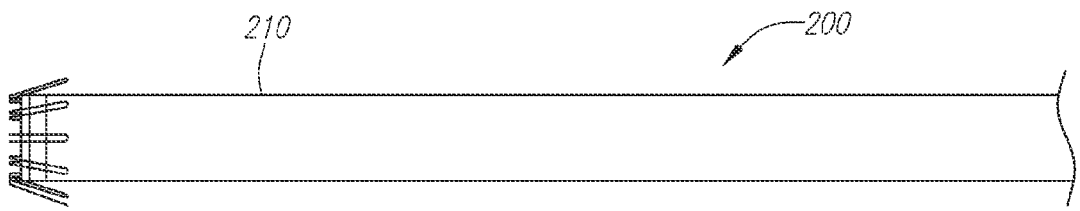
FIGS. 5A-5E illustrate progressive stages of stent frame deployment and recapture for a second embodiment.
Figure 5B:
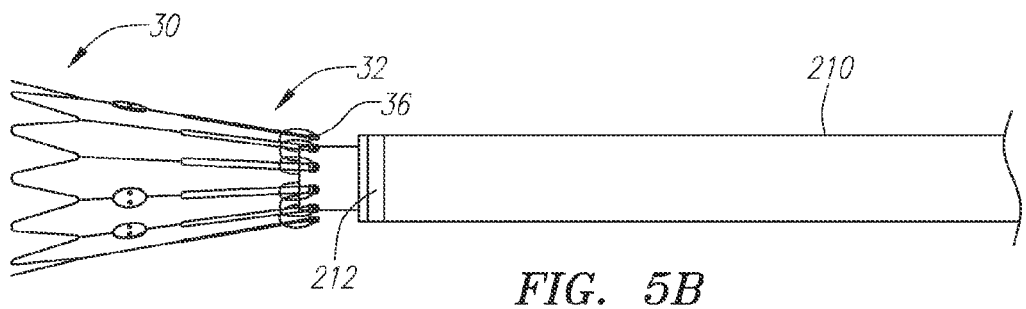
Figure 5C:
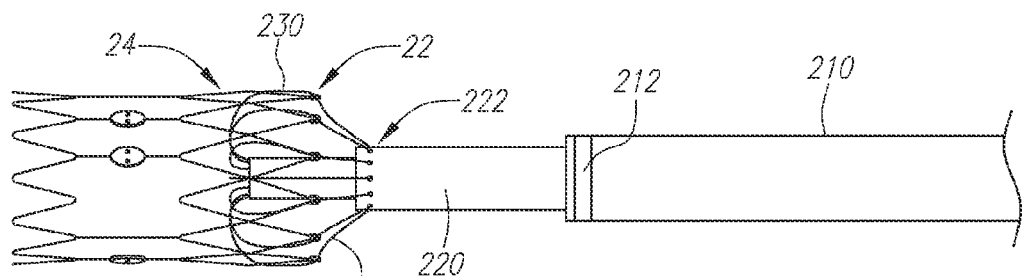
Figure 5D:
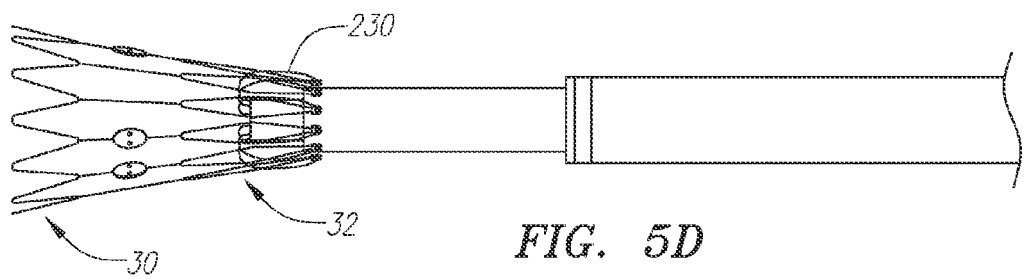
Figure 5E:
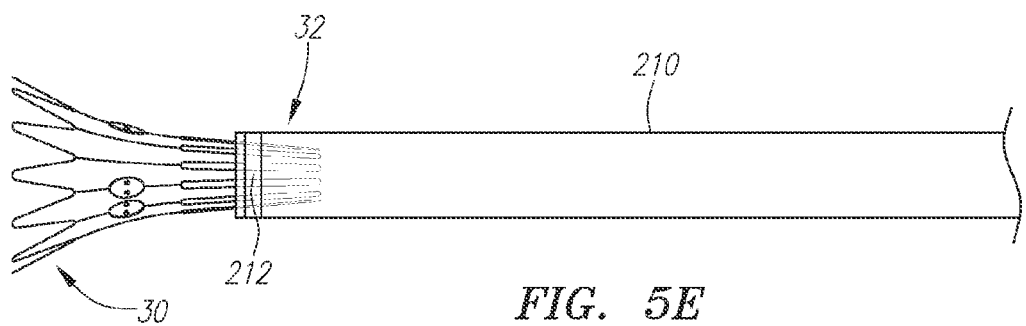

FIGS. 5A-5E illustrate a range of activity that is possible in terms of device manipulation before such release. In succession, these views show progressive stent frame deployment and steps toward complete recapture. FIG. 5A pictures (literally, given that the figures are based on photographs) the beginning of stent frame deployment as sheath 210 is withdrawn and a distal end 30 of the stent self-expands. FIG. 5B shows the sheath fully withdrawn and full tension on the draw lines or filaments, maintaining a proximal side 32 of the stent 20 in a compressed state. As in FIG. 5D illustrating the same (but in the case of FIG. 5D re-compression after the relaxation of draw lines to allow expansion as in FIG. 5C), the sheath can be advanced to fully recapture the stent frame. With the beginning of such action shown in FIG. 5E, the stent frame can be fully recovered within sheath 210—whether for the purpose of repositioning or bulk retrieval of the device.

A third delivery device embodiment is able to offer similar advantages in terms of delivery, repositioning, and/or percutaneous retrieval. Stent frame components of such a system are shown in FIGS. 11A and 11B. In each view, a proximal end 32 of a stent frame 20 includes clasp features 40. Each clasp feature 40 may comprise a bridge section 42 and an overhang section 44. Complementary clasp features 50 are provided at the end of resilient retainer "arms" or "fingers" 52 associated with a delivery system pusher. Arms 52 may comprise Nitinol or another elastic or superelastic material. Arms 52 are biased outward such that they spring out to a position as shown in FIG. 12 when released from restraint (e.g., upon exiting a delivery system sheath element or delivery/guide catheter body). Arms 52 are joined or meet at a hub 54. These components may be cut from a single hypotube or polymer sleeve that extends to the proximal end of the delivery system (not shown) as one piece or be assembled using conventional techniques such as laser welding, etc. In any case, pairs of complementary clasp elements 40/50 are releasably engaged in sheaths 60.

FIGS. 13A and 13B illustrate a construct in which multiple sheaths 60 extend to and join at a hub 62 optionally extending proximally as a single sleeve 64. Such a structure can be produced by bundling and reconfiguring (e.g., by fusing) a plurality of thermoplastic sheaths, bundling and bonding a plurality of sheaths, and splitting an end of a multi-lumen extrusion into a plurality of separate sheaths. Other means of construction will be appreciated by those of skill in the art as well.

Figure 14A:
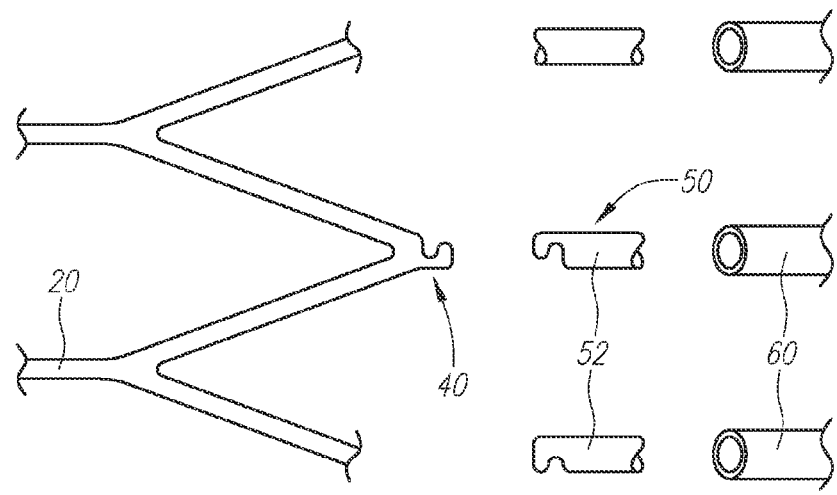
FIG. 14A illustrates segments of an expanded heart valve frame, retainer fingers, and zip tube fingers as associated in the subject embodiment
Figure 14B:
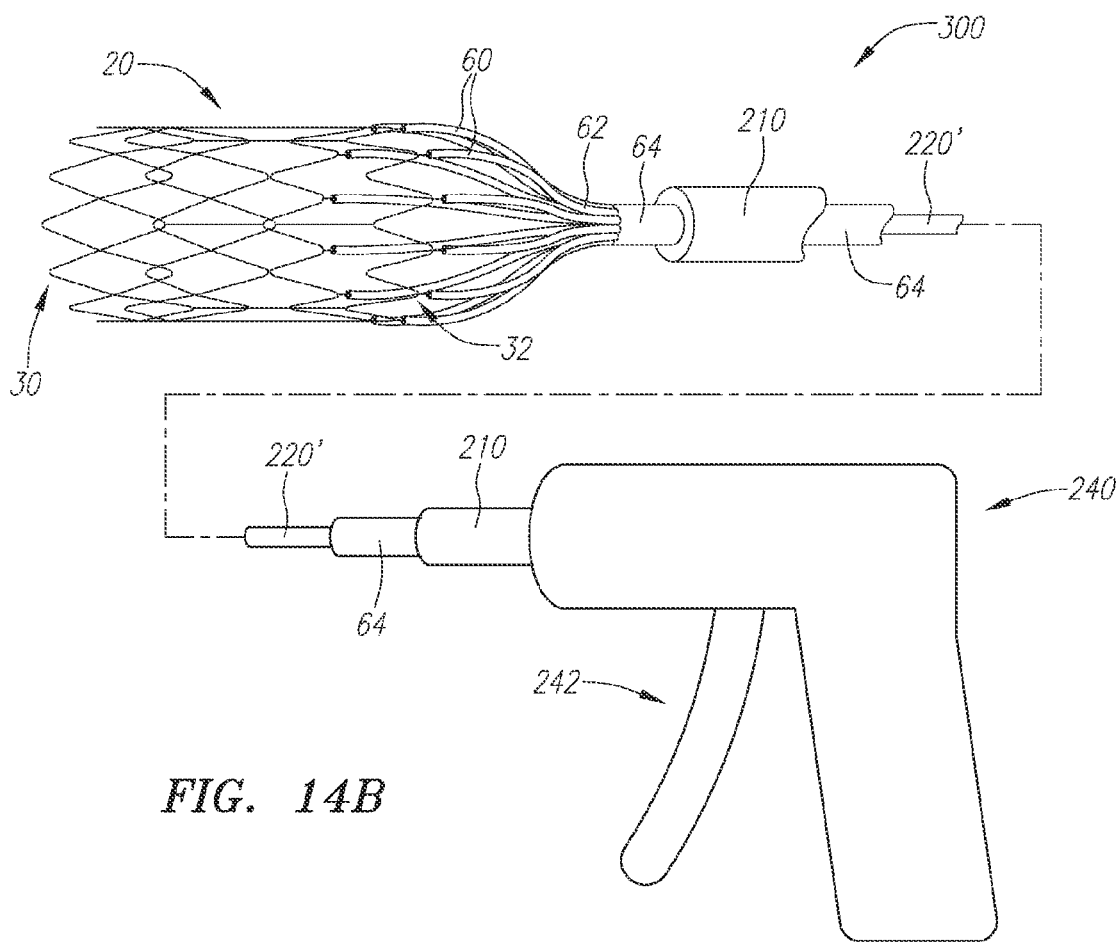
FIG. 14B illustrates a complete assembly of the embodiment including these subcomponents.

Regardless, FIG. 14A provides a partial assembly drawing illustrating the axial alignment for a plurality of interfacing members. FIG. 14B shows the same components of the third device embodiment brought together in a completed apparatus assembly 300. As in the embodiments above, such a system may optionally include a cover sheath 210 and a handle 240. In addition, system 300 may include an innermost elongate sleeve 220' optionally providing a lubricious PTFE liner for a guidewire lumen and/or column or "push" strength to the system.

Figure 15A:
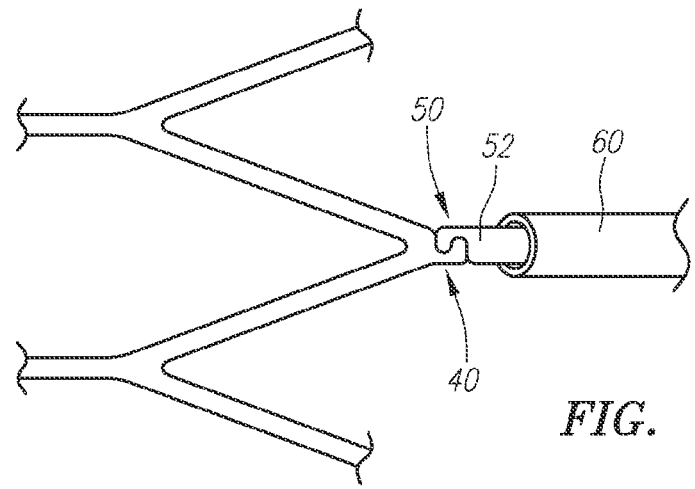
FIGS. 15A-15F are detail side views illustrating operation of elements within the embodiment.
Figure 15B:
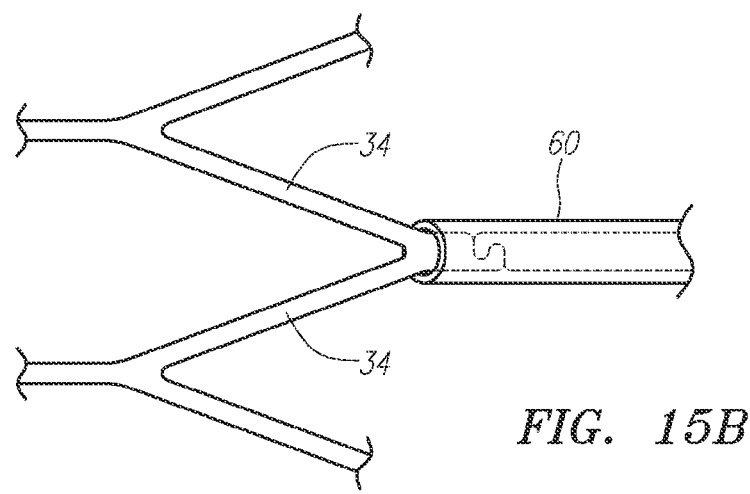
Figure 15C:
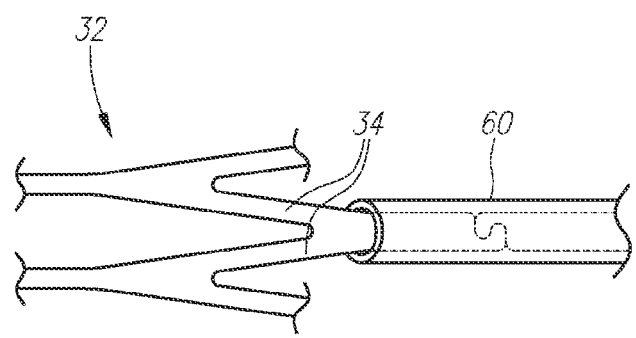
Figure 15D:
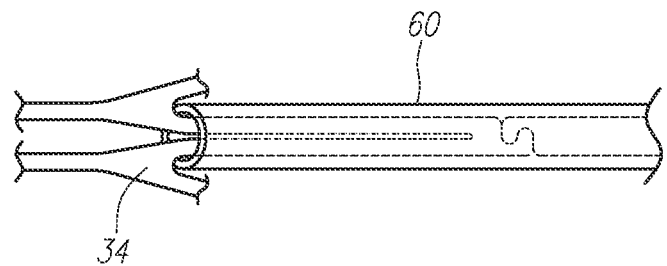
Figure 15E:
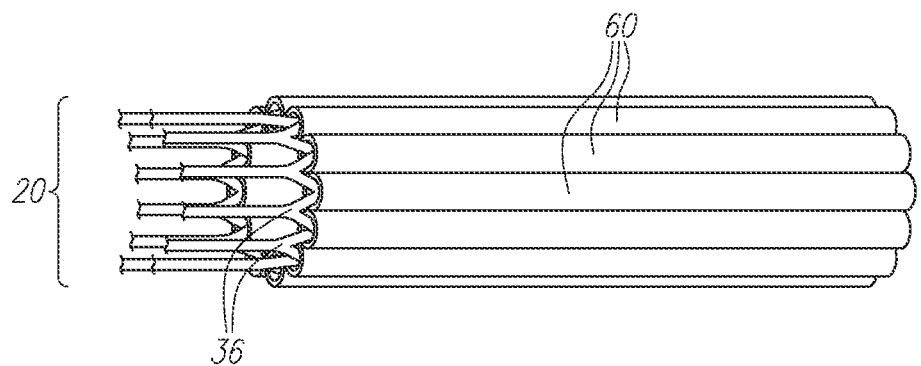

FIGS. 15A-15F illustrate the operation of an intended interaction of the subcomponents of system 300. In FIG. 15A, the heart valve frame clasp or link 40 is interfaced with clasp/line 50. In FIG. 15B, clasps features 40/50 are trapped within sheath 60. At this point, further withdrawal of stent frame 20 into sheath element 60 or (stated otherwise) advancement of sheath 60 over adjacent proximal stent struts 34 results in a condition as shown in FIG. 15C. Here, struts 34 are brought together collapsing the entirety of the proximal end 32 of stent frame 20 (given that the same condition is achieved around the entire periphery of the stent by paired device features). As shown in FIG. 15D, sheath 60 can cover the entirety of struts 34 up to their junctions 36 with adjacent struts. The net effect is shown in FIG. 15E where the entire proximal side of the stent frame 20 is compressed efficiently by the multiple sheath elements shown.

As summarized above, the zip tub part assembly (sheaths 60 and associated components) may be variably retracted to allow the proximal end 32 of the stent frame to partially expand or retracted sufficiently to allow the stent frame to fully expand. Alternatively, the zip part/assembly may be secured in position and the arm retainer 54 retracted to variably collapse the proximal end of the heart valve device (up to fully collapsed) or variably advanced to allow the self-expanding heart valve device to variably expand (up to fully expanded). Further action associated with collapse/compression and expansion of the stent frame is achieved by covering and uncovering the stent frame with optional sheath 210 or by a guide catheter.

Figure 15F:
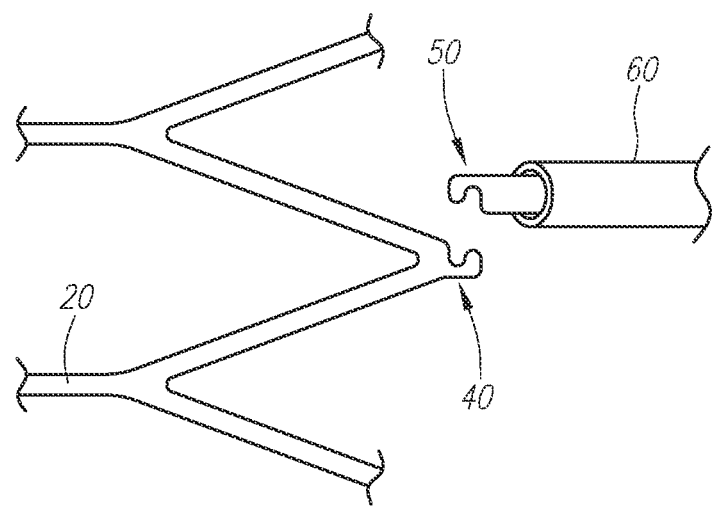

In any case, upon achieving desired implant placement, clasp elements 40/50 can be freed from confinement within the sheath member(s) 60 thereby unlinking the elements allowing stent frame 20 release as shown in FIG. 15F and allowing delivery system withdrawal from a patient in a successful percutaneous heart valve implantation procedure.

Figure 16A:
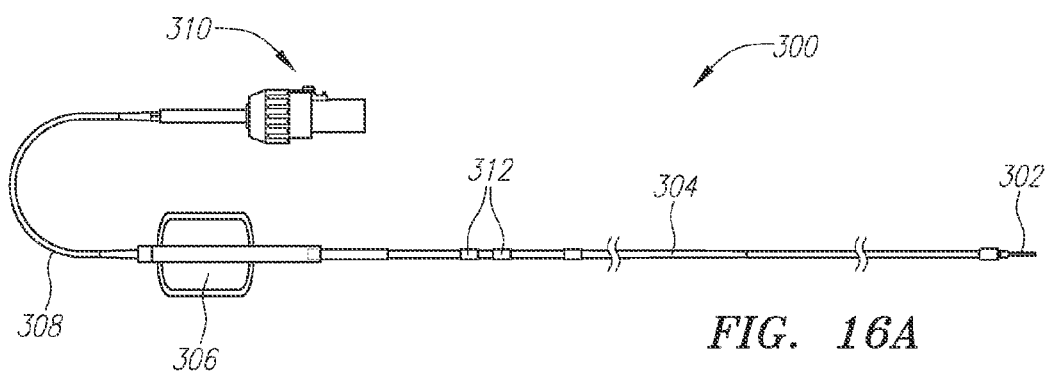
FIGS. 16A and 16B are side views illustrating an example embodiment of imaging catheter and stent frame components of an imaged-guided delivery system.

FIG. 16A illustrates a suitable IVUS catheter 300 for use in an image-guided valve delivery system according to another embodiment. The figure shows an EAGLE-EYE IVUS imaging catheter (Volcano Corp). Imaging catheter 300 includes a distal transducer tip 302, an intermediate catheter shaft or body 304, handle/grip 306, lead 308, and a proximal connector 310. Radiopaque shaft markers 312 are provided that may be relocated or additional markers added for coordination with a valve delivery catheter to (together) provide an overall valve delivery catheter system (e.g., by inserting catheter 300 within delivery system 100 or 200 as previously illustrated).

Figure 16B:
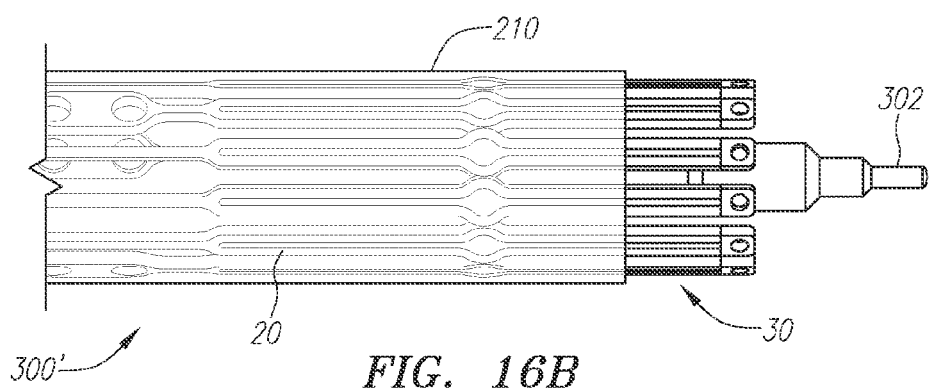

A distal portion of such a combined system 300' in shown in FIG. 16B. This photograph shows a distal end 30 of a TAVR stent 20 compressed to 4.3 mm diameter (13Fr). It is held in a sheath 210 that may form part of an overall delivery system 300'. Otherwise, it may be regarded as a loading sheath or surrogate (or stand-in) for a delivery catheter through which the stent 20 will track in a medical procedure. As shown, an ATLANTIS SR PRO IVUS transducer (Boston Scientific Corp.) 302 is placed through the center of the valve stent frame 20 for sizing purposes.

The image does not show the valve leaflets (e.g., as in FIGS. 1A-1F) for the overall implant that contribute to the inner diameter space constraints or the specific delivery system features that may be employed. Yet, the image illustrates the general hardware (stent frame, delivery system/sheath components and IVUS device) that may be employed in the subject systems and methods.

Figure 17:
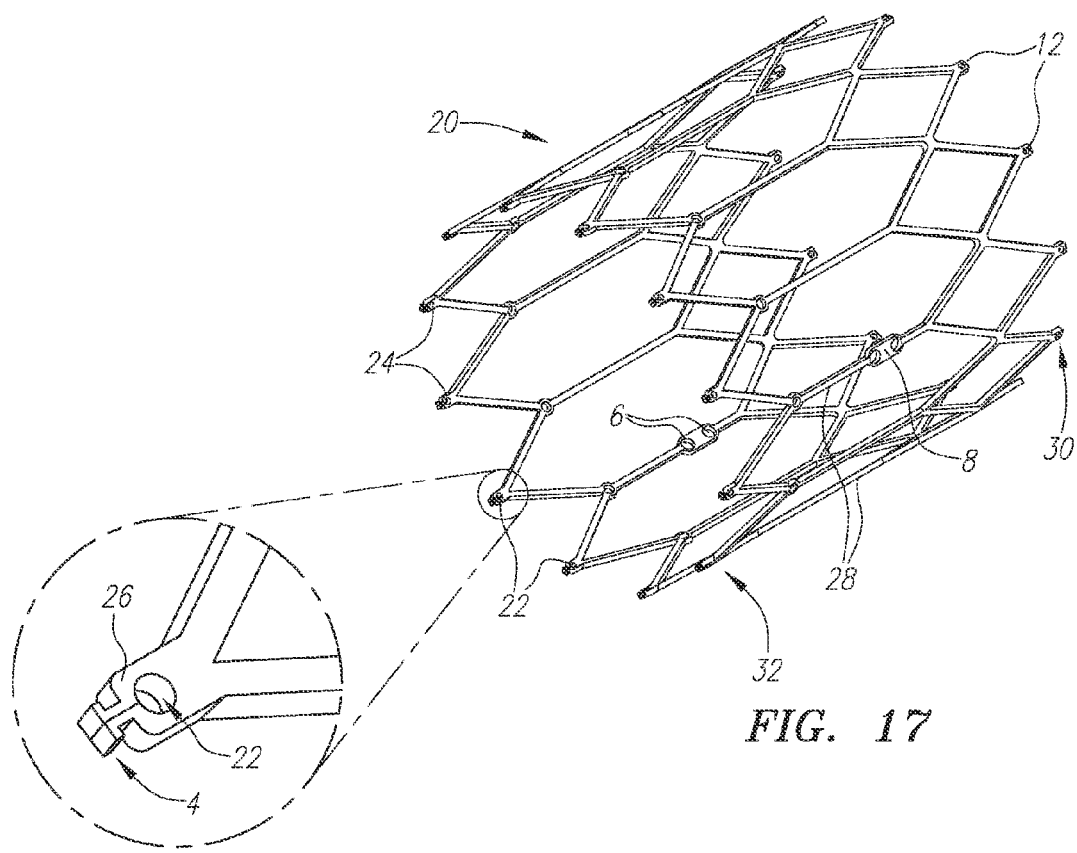
FIG. 17 is an enlarged perspective view of a stent frame component as previously illustrated.

FIG. 17 is a perspective view of a stent frame 20 component that may be employed therein. Actually, this figure provides an enlarged view of the stent frame shown in FIGS. 7A and 7B. So-enlarged, features in addition to those of the stent in U.S. Pat. No. 8,133,270 upon which the overall architecture may be based are easily highlighted. Specifically, two sets of holes 22 and 24 (proximal and more distal) are provided at the proximal side 32 of the stent frame 20 (i.e., on the "top" of the stent that would be positioned in the aortic root). These holes allow for passage of a network of pull-strings or filaments used for step-wise deployment, repositioning of the stent, and retrievability back to the guide-wire catheter (as discussed above) and also lateral positioning (as discussed below). Further, T-shaped structures 4 at the proximal side 32 are added to proximal crown features 26 to accommodate repositioning and retrievability of the valve during implantation procedure by way of attachment to complimentary delivery system features 40 like the example shown in FIGS. 14A and 14B.

In addition, connector holes 6 in tabs 8 of material at the middle of a number of struts 28 are provided to accommodate locking with pin-shape structures that permanently affix/connect the valve 10 material to the stent frame structure as further described in U.S. patent application Ser. No. 13/773,389 filed Feb. 21, 2013, which application is incorporated by reference herein in its entirety. A set of distal holes 12 at distal end 30 or "bottom" ventricular side of the stent advantageously provide attachment points (e.g., by suturing) of the valve leaflets to the stent frame as illustrated in FIGS. 1A-1F.

FIGS. 18A and 18B are side views of the same stent frame 20 associated with a delivery system 200' related to that in FIGS. 5A-10B, but including additional manipulation features. Specifically, delivery system 200' is adapted for controlling the lateral position of a heart valve device, for positioning or repositioning during deployment. Draw lines (or filaments) 230 (configured as in the referenced embodiments) are further connected to a pivot fitment 250 and a joystick-type handle 252.

Figure 19A:
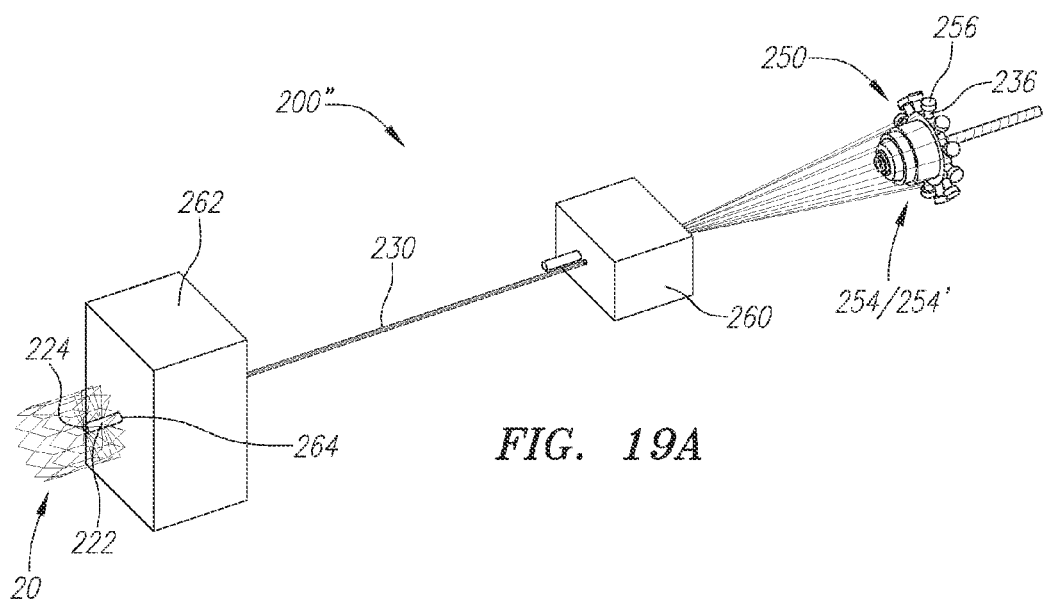
FIGS. 19A and 19B are photographs illustrating prototype hardware of the delivery system embodiment diagrammatically illustrated in FIGS. 18A and 18B.
Figure 19B:
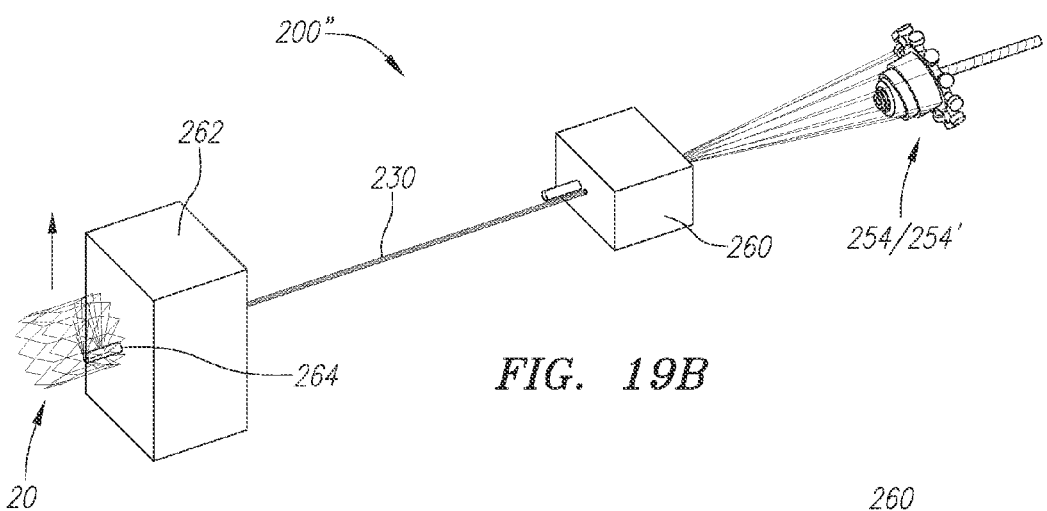

As shown in FIGS. 19A and 19B loops or end ties 236 around spurs 256 may provide such a connection. As likewise shown, fitment 250 (alternatively, a boss, cap or housing) may ride upon or otherwise incorporate one or more spherical bearing surfaces 254/254'.

However configured, operation of system 200' is such that the angular ordering of the draw lines 230 in the overall heart valve (stent frame 20 shown) will correspond to the angular ordering of the draw lines on pivot fitment 250. Such activity is assured by the corresponding relationship of draw lines (or filaments) as shown in cross-sections A-A and B-B in FIG. 18A. The radial orientation of filaments 230 at the stent frame 20 and leading to the stent frame are matched with the radial orientation of the filaments at fitment 250 is indicated by the matching numeral position in the two cross-sectional views.

Therefore, as shown in FIG. 18B, tilting the pivot fitment 250 (e.g., by leaver arm/joystick 252) causes coordinated pull and release (or relaxation) of the draw lines proportional to the angular ordering and the direction of tilt to drive a corresponding change in the lateral position of the heart valve device (denoted by the directional arrows). Thus, the lateral position of the heart valve device can be controlled and manipulated by tilting the pivot fitment. While a joystick or similar interface can be incorporated into or connected to the pivot fitment to facilitate control of the tilt mechanism, other approaches including remote/robotic control are contemplated as well.

In any case, FIGS. 19A and 19B are photographs of a functional prototype 200" of the delivery system embodiment diagrammatically shown in FIGS. 18A and 18B. Here, blocks 260, 262 simulate the end constraint conditions of a catheter body. Between these, filaments 230 are visible (whereas they would generally be housed within a catheter body/sleeve). A short sleeve 264 extends from block 262 to simulate the distal portion of the catheter body 220 shown in FIGS. 5A-10B, 18A and 18B including its side apertures 222 and an end hole 224.

In FIG. 19A, stent frame 20 and pivot fitment 250 are shown in a neutral or "home" position. While being tilted/turned, as shown in FIG. 19B, pivot fitment 250 reorients the filaments 230 to move stent 20 laterally in relation to sleeve 264.

Figure 20:
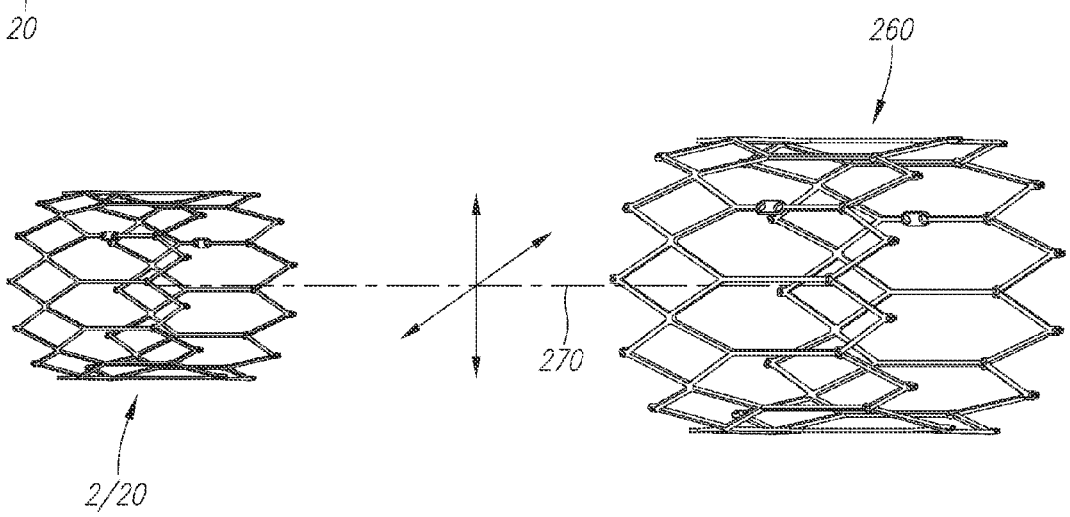
FIG. 20 diagrammatically illustrates an alternative user interface for the FIGS. 18A and 18B delivery system.

Finally, FIG. 20 diagrammatically illustrates an alternative user interface for the FIGS. 18A and 18B delivery system. Here, instead of using a handle, a model 260 of the implant 2 (or at least the stent frame 20) to be delivered is employed. The model may be a scale replica of the stent frame 20 and/or the entire implant 2. Generally, it will be configured in an expanded shape. However, it may be controlled so that its state of expansion matches that of implant 2. Alternatively, manipulation of the model expansion may alter the expansion state of the implant. Given all of these options, however, the model will generally at least serve as an interface for lateral valve positioning.

In which case, the model may be connected to the filaments in the same manner/fashion as the stent frame 20 to be manipulated along a catheter centerline 270 by movement of the model in any combination of lateral directions indicated by the axis arrows shown. Alternatively, model 260 may overlay and be connected to fitment 252 to which the filaments are connected (e.g., at spurs 254).

Use of the model 260 in manipulating the stent frame 20 and being able to visualize the direct correspondence of movement between the implant (via fluoroscopy or other medical imaging) to the sight of the model in hand may be particularly beneficial to a physician in attempting ideal implant positioning and placement. In a method of use, the method may comprise at least partially deploying stent frame 20 by withdrawing a sheath 210 covering the stent frame and relaxing the filaments 230 passing through a catheter sleeve 220 and attached to the stent frame to expand the stent frame (e.g., as in such activity shown in FIGS. 5A-5C). Then, a proximal interface such as a joystick or model is manipulated to move the stent frame laterally relative to the catheter sleeve by selectively tightening and relaxing the filaments (e.g., as in such activity shown in FIG. 18B relative to a zero or neutral position of fitment 252). Naturally, the device can be returned to center and then recompressed and/or resheathed for repositioning as well.

In the various delivery system architectures, the catheter/pusher shaft or sleeve may comprise a simple extrusion (e.g., PTFE, FEP, PEEK, PI etc.) or may be constructed using conventional catheter construction techniques and include a liner, braid support and outer jacket (not shown). Likewise, the various tubular members may comprise extrusion (per above), metal hypotube, etc. Further, the stent frame may be constructed using conventional laser cutting and electropolishing techniques and/or be otherwise constructed. In embodiments intended for tracking through a guide/delivery catheter without an incorporated sheath, a loading sheath (optionally peel-away or splittable) may be provided over the implant. Other typical percutaneous access instruments (such as wires, etc.), valves, and other hardware may also be employed in connection with the subject matter described herein.

The subject methods may include each of the physician activities associated with implant positioning, re-positioning, retrieval and/or release. Regarding these methods, including methods of manufacture and use, these may be carried out in any order of events which is logically possible, as well as any recited order of events.

Furthermore, where a range of values is provided, it is understood that every intervening value, between the upper and lower limit of that range and any other stated or intervening value in the stated range is encompassed within the invention. Also, it is contemplated that any optional feature of the described variations may be set forth and claimed independently, or in combination with any one or more of the features described herein.

Reference to a singular item includes the possibility that there are a plurality of the same items present. More specifically, as used herein and in the appended claims, the singular forms "a," "an," "said," and "the" include plural referents unless specifically stated otherwise. In other words, use of the singular forms allow for "at least one" of the subject item in the description above as well as the claims below. It is further noted that the claims may exclude any optional element and may explicitly limit each element to a "single" instance or "only one" such instance of that element. As such, this paragraph is intended to serve as antecedent basis for the use of such exclusive terminology as "solely," "only," "a single" and the like in connection with the recitation of claim elements, or the use of a negative limitation.

Without the use of such exclusive terminology, the terms "comprising," "including," and "having" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the different embodiments or aspects described herein is not to be limited to the examples provided and/or the subject specification, but rather only by the scope of the issued claim language.

The invention claimed is:

1. A medical device comprising:
   an elongate sleeve having a distal end and a proximal end;
   a plurality of apertures in the sleeve adjacent the distal end;
   an elastic stent frame comprising a plurality of struts, each strut including a proximal aperture,
   wherein the proximal aperture in each strut together form a plurality of proximal apertures of the stent frame,
   wherein the stent frame further comprises a plurality of distal apertures, each distal aperture being in one of the plurality of struts of the stent frame; and
   a plurality of filaments, each filament received within the sleeve from the proximal end, passing out of and looping over the sleeve, passing through one of the strut distal apertures, running directly along a length of one of the struts, passing through one of the strut proximal apertures, and passing through one of the sleeve apertures and into the sleeve.

2. The device of claim 1, further comprising a valve connected to the stent frame.

3. The device of claim 1, wherein the sleeve comprises a distal proximal shoulder for abutting the stent frame during advancement.

4. The device of claim 1, further comprising a sheath to cover the stent frame.

5. The device of claim 4, where the sheath is connected to a handle adapted to advance the sheath to cover the stent frame or retract the sheath to uncover the stent frame.

6. The device of claim 5, wherein the handle is adapted to select and actuate the sheath to intermediate states between full advancement and full retraction.

7. The device of claim 6, wherein retraction of the sheath allows a distal end of the stent frame to expand, and advancement of the sheath compresses the distal portion of the stent frame.

8. The device of claim 1, wherein two ends of each filament pass through the proximal end of the sleeve.

9. The device of claim 8, wherein the two ends of each filament are connected to a handle adapted to actuate the filaments.

10. The device of claim 9, wherein the handle is adapted to select and actuate a proximal portion of the stent frame between states of full expansion for deployment and full compression for retrieval.

11. The device of claim 10, wherein the handle is adapted to select and actuate the proximal end of the stent frame to intermediate states between full compression and full expansion.

12. The delivery system of claim 1, further comprising a handle at the proximal end, the handle including a pivot fitment, the filaments connected to the pivot fitment spaced in a radial orientation matching a radial orientation of the filaments at the stent frame.

13. The delivery system of claim 12, wherein the pivot fitment rides on a spherical bearing surface.

14. The delivery system of claim 12, further comprising a joystick to actuate the fitment.

15. The delivery system of claim 12, further comprising an implant model to actuate the fitment, the model at least substantially resembling the stent frame in appearance.

16. The delivery system of claim 15, wherein the model is a scale replica of the stent frame in an expanded state.

17. A medical device delivery system comprising:
an elongate sleeve having a distal end and a proximal end, a plurality of apertures in the sleeve adjacent the distal end;
an elastic stent frame comprising a plurality of struts, each strut including an aperture, wherein the aperture in each strut together form a plurality of proximal apertures of the stent frame, wherein the stent frame further comprises a plurality of distal apertures, each distal aperture being in one of the plurality of struts of the stent frame;
a plurality of filaments, each filament received within the sleeve from the proximal end, passing out and looping over the sleeve, passing through one of the proximal strut apertures, directly running along the length of one of the struts to, and passing through one of the distal apertures, and passing through one of the sleeve apertures and into the sleeve; and
a handle at the proximal end, the handle including a pivot fitment, the filaments connected to the pivot fitment spaced in a radial orientation matching a radial orientation of the filaments at the stent frame.

18. The delivery system of claim 17, wherein the filaments pass out of the distal end of the sleeve.

19. The delivery system of claim 17, wherein the pivot fitment rides on a spherical bearing surface.

20. The delivery system of claim 17, further comprising a joystick to actuate the fitment.

21. The delivery system of claim 17, further comprising an implant model to actuate the fitment, the model at least substantially resembling the stent frame in appearance.

22. The delivery system of claim 21, wherein the model is a scale replica of the stent frame in an expanded state.

* * * * *